(12) United States Patent
Padate et al.

(10) Patent No.: US 8,788,287 B2
(45) Date of Patent: Jul. 22, 2014

(54) SYSTEMS, APPARATUS, AND METHODS FOR DEVELOPING PATIENT MEDICAL HISTORY USING HIERARCHICAL RELATIONSHIPS

(75) Inventors: Priya Balvant Padate, Palatine, IL (US); Ashish Vassa, Palatine, IL (US); Jeff Chu, Buffalo Grove, IL (US); Nikhil Jain, Barrington, IL (US); George Brown, Boston, MA (US)

(73) Assignee: General Electric Company, Schenectady, NY (US)

( * ) Notice: Subject to any disclaimer, the term of this patent is extended or adjusted under 35 U.S.C. 154(b) by 654 days.

(21) Appl. No.: 12/626,385

(22) Filed: Nov. 25, 2009

(65) Prior Publication Data

US 2011/0125528 A1    May 26, 2011

(51) Int. Cl.
*G06F 17/30* (2006.01)
*G06Q 50/00* (2012.01)

(52) U.S. Cl.
USPC ..................................... 705/3; 707/10; 707/3

(58) Field of Classification Search
USPC .............................................................. 705/3
See application file for complete search history.

(56) References Cited

U.S. PATENT DOCUMENTS

| 4,501,559 | A | 2/1985 | Griswold et al. |
| 6,760,731 | B2 | 7/2004 | Huff |
| 2002/0010597 | A1 | 1/2002 | Mayer et al. |
| 2002/0023097 | A1* | 2/2002 | Ripley .......................... 707/200 |
| 2006/0117021 | A1* | 6/2006 | Sidney et al. ................... 707/10 |
| 2006/0173717 | A1 | 8/2006 | Scheuner |
| 2008/0091463 | A1 | 4/2008 | Shakamuri |

* cited by examiner

*Primary Examiner* — Hiep V Nguyen
(74) *Attorney, Agent, or Firm* — Hanley, Flight & Zimmerman, LLC.

(57) ABSTRACT

An example apparatus provides access to electronic health information for a first patient and one or more patients connected by relationship to the first patient. A first patient indicator represents a first patient and provides a link to electronic health information for the first patient. A second patient indicator represents a second patient and provides a link to electronic health information for the second patient. A connection provides a graphical indication of a relationship between the first patient and the second patient and connects electronic health information for the second patient for access in connection with electronic health information for the first patient. The connection is to provide a graphical indication of a priority of the relationship between the first patient and the second patient based on a defined relationship hierarchy. A graphical indication of a type of relationship between the first patient and the second patient is provided.

20 Claims, 14 Drawing Sheets

SYSTEMS, APPARATUS, AND METHODS FOR DEVELOPING PATIENT MEDICAL HISTORY USING HIERARCHICAL RELATIONSHIPS

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND

The present disclosure generally relates to systems, methods, apparatus, and articles of manufacture to process electronic patient information. More particularly, certain examples provide systems, methods, apparatus, and articles of manufacture to provide access to and graphical representations of relationships between patients and link electronic information related to those patients.

Healthcare environments, such as hospitals or clinics, include information systems, such as hospital information systems (HIS), radiology information systems (RIS), clinical information systems (CIS), and cardiovascular information systems (CVIS), and storage systems, such as picture archiving and communication systems (PACS), library information systems (LIS), and electronic medical records (EMR). Information stored may include patient medical histories, imaging data, test results, diagnosis information, management information, insurance information, and/or scheduling information, for example. The information may be centrally stored or divided at a plurality of locations. Healthcare practitioners may desire to access patient information or other information at various points in a healthcare workflow.

Efforts are underway nationally to connect healthcare information systems and make them interoperable in a secure, sustainable, and standards-based manner. However, the required information infrastructure is still under development, both for the National Health Information Network (NHIN) led by the federal government, as well as for the many small Regional Health Information Organizations (RHIOs) across the nation. Many challenges remain for health information exchange in the United States and elsewhere. Additionally, there is a need for standardization and interoperability of healthcare information among participants in exchange networks. Furthermore, there is a need for systems providing centralization versus distributed data architectures.

In the current medical environment, access to patient medical records is cumbersome and fragmented. Typically, medical records are maintained at individual clinics. If a patient visits more than one clinic, a patient may have a plurality of medical records. For example, a patient may visit a first clinic and create a first medical record and the patient may subsequently visit a second clinic and create a second medical record. If the second clinic does not have access to the first medical record, the examination and diagnosis at the second clinic may be duplicative and inefficient.

The lack of comprehensive medical records is also duplicative and inefficient for the patient. For example, a patient typically fills out similar forms at each clinic the patient attends. The patient may fill out a form with the patient's medical history, various conditions, allergies, heredity information, or other information. The individual clinic then maintains their own record for the patient. As a patient may visit a plurality of clinics in his or her life, the patient may repeatedly fill out the same information. In some circumstances, the patient may not fill out the same information, and various medical records at different clinics may contain partial and/or out-of-date information.

In addition, the decentralized nature of patient medical record information is perpetuated by entities other than medical clinics. For example, medical record information may be maintained by insurance entities, pharmaceutical entities, and/or laboratory entities. An update of the patient medical record at any one of these entities does not ensure the other entities are updated. Accordingly, the patient medical record information differs depending on the entity. Accordingly, it is difficult to locate a medical record that is completely up-to-date, and a treating physician may not be able to obtain a complete picture of a patient's health prior to treatment. Additionally, as a consequence of patient information being decentralized and a patient not having access to his or her patient medical record information, the information available to a patient regarding his or her health status is typically of a general nature.

SUMMARY

Certain examples provide systems, methods, apparatus, and articles of manufacture to provide access to and graphical representations of relationships between patients and link electronic information related to those patients.

In some examples, an apparatus provides access to electronic health information for a first patient and one or more patients connected by relationship to the first patient. The apparatus includes a first patient indicator representing a first patient and providing a link to electronic health information for the first patient, the electronic health information to be accessible to a user by selecting the first patient indicator. The apparatus includes a second patient indicator representing a second patient and providing a link to electronic health information for the second patient. The apparatus includes a connection providing a graphical indication of a relationship between the first patient and the second patient and connecting electronic health information for the second patient for access in connection with electronic health information for the first patient. The connection is to provide a graphical indication of a priority of the relationship between the first patient and the second patient based on a defined relationship hierarchy. The apparatus includes a graphical indication of a type of relationship between the first patient and the second patient. The first patient indicator, the second patient indicator, the connection, and the graphical relationship indicator are displayed for user interaction together on a display via a user interface.

In some examples, a tangible computer-readable storage medium includes a set of instructions for execution on a processor. The set of instructions, when executed, implement a system for graphical display of and access to electronic health information for a first patient and one or more patients connected by relationship to the first patient. The system includes a first patient indicator representing a first patient and providing a link to electronic health information for the first patient, the electronic health information to be accessible to a user by selecting the first patient indicator. The system includes a second patient indicator representing a second patient and providing a link to electronic health information for the second patient. The system includes a connection providing a graphical indication of a relationship between the first patient and the second patient and connecting electronic health information for the second patient for access in connection with electronic health information for the first patient. The connection is to provide a graphical indication of a priority of the relationship between the first patient and the second patient based on a defined relationship hierarchy. The system includes a graphical indication of a type of relationship between the first patient and the second patient. The first patient indicator, the second patient indicator, the connection, and the graphical relationship indicator are displayed for user interaction together on a display via a user interface.

In some examples, a computer-implemented method for graphically displaying and providing access to electronic health information for a first patient and one or more patients connected by relationship to the first patient. The method includes generating and displaying a first patient indicator representing a first patient and providing a link to electronic health information for the first patient, the electronic health information to be accessible to a user by selecting the first patient indicator. The method includes generating and displaying a second patient indicator representing a second patient and providing a link to electronic health information for the second patient. The method includes providing a graphical indication of a relationship between the first patient and the second patient using a graphical connection between the first patient indicator and the second patient indicator and linking electronic health information for the second patient for access in connection with electronic health information for the first patient, the connection to provide a graphical indication of a priority of the relationship between the first patient and the second patient based on a defined relationship hierarchy. The method includes generating and displaying a graphical indication of a type of relationship between the first patient and the second patient. The first patient indicator, the second patient indicator, the connection, and the graphical relationship indicator are displayed for user interaction together on a display via a user interface.

Figure 1:
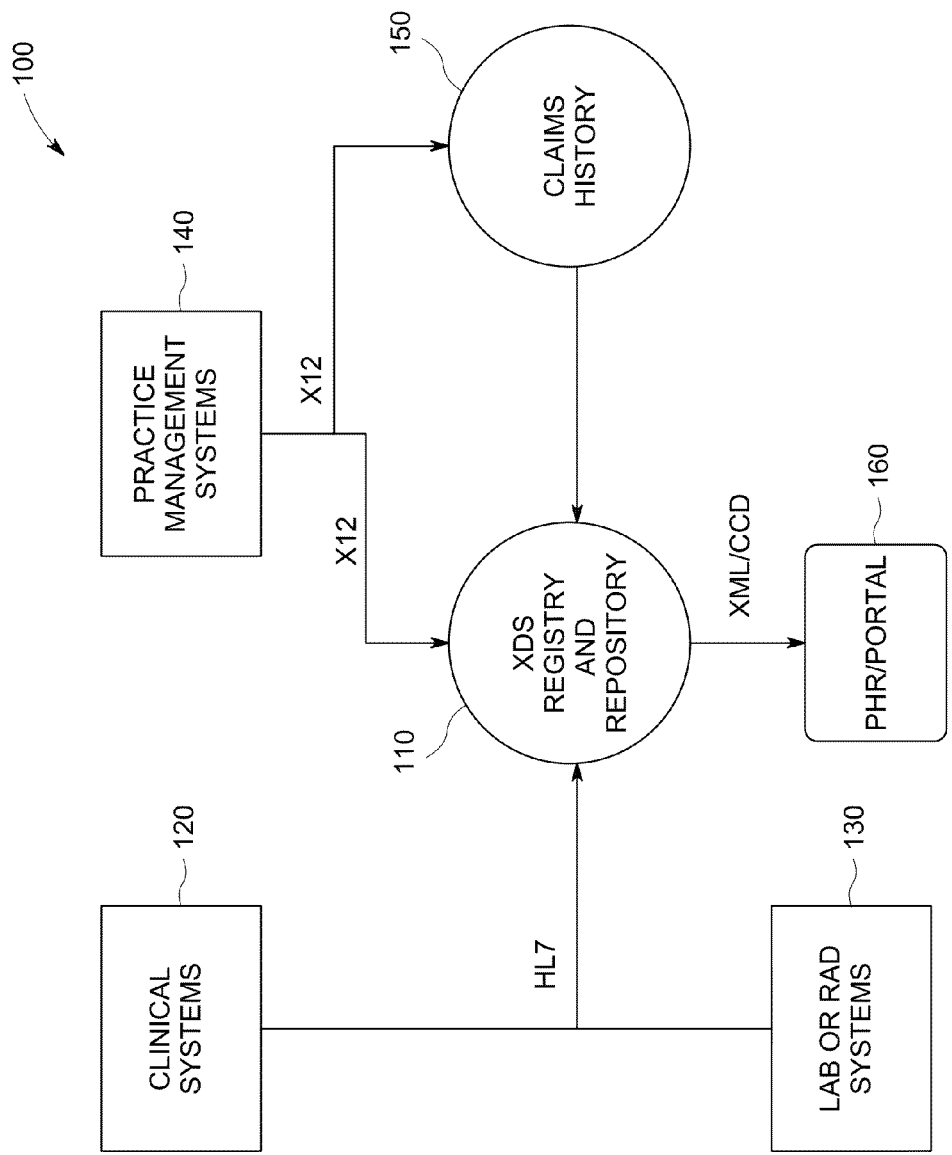
FIG. 1 illustrates an example healthcare information exchange (HIE).

The foregoing summary, as well as the following detailed description of certain example embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF CERTAIN EXAMPLES

Although the following discloses example methods, systems, articles of manufacture, and apparatus including, among other components, software executed on hardware, it should be noted that such methods and apparatus are merely illustrative and should not be considered as limiting. For example, it is contemplated that any or all of these hardware and software components could be embodied exclusively in hardware, exclusively in software, exclusively in firmware, or in any combination of hardware, software, and/or firmware. Accordingly, while the following describes example methods, systems, articles of manufacture, and apparatus, the examples provided are not the only way to implement such methods, systems, articles of manufacture, and apparatus.

When any of the appended claims are read to cover a purely software and/or firmware implementation, at least one of the elements of at least one example is hereby expressly defined to include a tangible medium such as a memory, a digital video disc (DVD), compact disc (CD), etc. storing the software and/or firmware.

A hospital enterprise and/or other clinical environment can maintain much information about patients to which the enterprise provides services. Many registered patients are interrelated by a set of defined relationships. The hospital or other environment may not have complete information of such relationships between clients. By capturing the relationship information, hereafter referred as Patient-to-Patient relationship (P2P) information, the hospital enterprise and the patients themselves can benefit from an increased body of information available, diagnosis and/or treatment suggestions, and/or other correlations to be made between information in related patient records, for example.

By taking advantage of available information, linked patients can be offered specialized, privileged services and/or can be tendered treatment at a discounted rate, for example, as a result of more efficient business plans and/or operating models. Shared and/or otherwise linked P2P information can be used for clinical analysis and/or surveys and other data collection, for example. P2P information can provide improved and/or expanded emergency contact information, for example.

Currently, family medical history information is collected from the patient during the registration process. This information is accurate only to the extent that the patient is aware of his/her family member's medical history. Family medical history information collected from the patient does not provide granular information, which can be helpful in future examination of the patient. Typically, registration information is collected once for a patient and is not updated as family members develop chronic diseases and/or other problems over time.

In certain examples, related patient records (e.g., electronic medical records, electronic health records, personal health records, etc.) and/or other electronic patient information can be identified as related. Related P2P information can be used in diagnosis, treatment, emergency contact, billing, and/or other clinical and/or administrative function with respect to a linked patient.

In certain examples, one or more systems, methods, apparatus, and/or articles of manufacture are provided to link a patient's unique identifier with his/her family members' identifiers to build a family medical history. The family medical history can be used, for example, to better assist a patient with a family medical history of breast cancer, colorectal cancer, diabetes, heart disease, etc. The family medical history can also be of use for a pregnant mother concerned with prenatal care and genetics, for example. The family medical history can be a help to a medical practitioner in gathering information about the risk of disease development, if he/she had access to the detailed family medical history.

One or more disclosed systems, methods, apparatus, and/or articles of manufacture provide a mechanism to link different members of a family to share their medical records. Certain examples provide a registry where members are registered with a unique identifier, and each member can request a link to other family member by defining a unique hierarchical relationship with him/her. For example, John Doe can enter his information in the registry and can request link to his family members, Jane Doe (Sister), Jeff Doe (Paternal uncle), Joanna Doe (Mother). The items in parentheses identify a hierarchical relationship between John Doe and the other person.

Certain examples provide access to medical records after consent is obtained from patient's family members and/or other linked individuals. Consent can be obtained on a per event basis, periodically, and/or as a one-time question (e.g., upon linking, upon providing a suggestion to link, etc.), etc. In some examples, rather than allowing the patient to directly access his family members' medical records, linked information can be made available anonymously, automatically provided to a clinical system for assist in diagnosis, treatment, and/or other analysis, routed to an authorized care provider, etc. Anonymity of the information can be determined on record by record basis, for example.

In some examples, the patient is expected to be affiliated with affinity domain so that the patient can share medical records and establish links. An affinity domain is a group of healthcare enterprises that have agreed to work together using a common set of policies and share a common infrastructure, for example.

Certain examples provide a patient identity source that generates unique patient identifiers. A hierarchical relationship is created to help a system, method, apparatus, article of manufacture and/or a clinician user of the system, method, apparatus, and/or article of manufacture to understand the significance of family member's medical history on patient's medical records. A patient registry is provided to register and link identifiers. Patient identifiers can also be used to pull and/or synchronize information among multiple sources. An affinity domain can be used to associate each patient. A consent mechanism is provided to obtain family member and/or other related individual approval to share medical records once a request to link is received. A document source such as a PACS, PHR, EMR, and/or other electronic data store, is provided to access the medical records.

By linking patients, a composite medical history can be generated. As a patient realizes a connection within his or her family and or other connected individual, he or she can gather more personal information regarding risk to develop particular diseases. With important information conveniently available to healthcare providers, a hospital can improve its efficiency in delivering care. A user can track and trend various information based on wide access to personal medical records collected from several sources of information.

In certain examples, a family medical history viewed at any given point includes all recent information regarding that patient's family members (that are participating in the link). Multiple data points in distributed systems such as an EMR, PHR, PACS, HIE, etc., can be brought together to assist in patient care. Certain examples can help a medical practitioner gather information about the risk of disease development based on access to a detailed family medical history. Certain examples provide a service offering for medical records linking across enterprises. Certain examples can be used to link people through medical records. Certain examples can be integrated with systems such as a PACS, RIS, PHR, EHR, HIE, etc., for medical records.

In some examples, a hierarchy is defined between linked patients and/or between characteristics and/or data related to those patients as found in their records. The hierarchy can be used to evaluate relevance of a condition found in the linked family history for patient diagnosis, for example.

In some examples, identifiers can be assigned to individual patients as well as to a family of connected patients. Patient identifiers can be cross-linked within a family. Cross-linking can be determined automatically and/or using a request and approval model, for example. Certain examples can search for family members and/or other relations for a patient, request a connection to the patient's record, and define a relationship between the patient and the other person. If the other person accepts, then the patient's record will reflect the other person's information as well.

An algorithm can be used to identify potential family member(s) based on a patient's record(s) and suggest a relationship to the patient. The algorithm can accommodate children of divorce, etc. The algorithm can be used to look for anyone that could be genetically influencing a patient's medical history and then ask one or more individuals if they want to connect. In some examples, a patient may have multiple identifiers across different systems; these identifiers can be cross-linked for the patient for reference across systems.

In some examples, Cross-enterprise Document Sharing (XDS) can be used to share and/or connect documents between facilities. XDS and Integrating the Healthcare Enterprise (IHE) profiles/protocols can be leveraged to transmit documents across facility systems and connect the documents for common use. A document format standard can be defined for searching and/or identifying information found in the documents, for example.

Cross-linking functionality can be built into a hospital revenue cycle management system and/or various patient information systems and/or can be supported from an independent system that gathers information from various patient information system applications that feed patient information into independent system, for example. Patient relationship information can be aggregated in a particular hospital information system and/or across several such systems, for example.

In certain examples, a graphical representation of a patient relationship tree can be provided to allow a user to more easily visualize patient relationships and/or other connections. Operators can be alerted to the relationship of a patient with other patients, for example, at various points in care, such as Admissions/Registration, Discharge, Transfer (ADT), etc., as configured by the operator, administrator, etc. Through graphical displays, alerts, etc., relationship information can be utilized for a patient during emergencies, for example. Relationship information can be used in clinical studies and analyses, for example. Relationship information can be used to provide input into hospital revenue cycle management systems to facilitate promotional campaigns, for example. Healthcare services can be improved, tailored, and/or otherwise better selected for patients based on their relationship and history information, for example. Health records organized based on link and relationship information can be provided and/or accessed as part of a patient-online portal, such as a personal health record portal accessible via the World Wide Web and/or private network.

Using electronic patient family history and/or other linked information can help clinicians provide improved patient care by enabling a supply of emergency contact information and supporting effective utilization of patient information, for example. Relationship information can help improve overall healthcare by providing information useful for clinical analysis. Linked information can be used to help generate customized care plans and organized care, as well as business opportunities within a hospital enterprise, for example.

Whereas patient information is often spread across systems without a way to identify and visualize relationships, patient relationships can be identified and depicted graphically, etc. Patient-to-patient relationships between a patient and his or her spouse, neighbor, social network, etc., can be identified, linked, tracked, depicted, etc. Information can be gathered from a variety of systems, such as by combing through and identifying information across databases. Patient-to-patient relationships can be displayed and/or otherwise graphically represented, for example.

Patient-to-patient relationship information and cross-linking can be implemented in conjunction with an EMR, PHR, and/or other connectivity framework, for example. Certain examples above may be applied to an architecture and components based upon Health Information Exchange (HIE) standards, such as document storage, querying, connectivity to data sources, data registry/repository, population-based clinical quality improvement and research database with reporting tools, hosted interfaces, master patient registry, master provider registry, etc. Combining cross-enterprise document sharing (XDS) with a clinical data repository (CDR) enables the original content and context of the documents to be preserved but also enables capture of clinically relevant values to enable other uses of the data beyond limitations of the document. Such combination may include normalization of data across data sources, for example. Certain examples also facilitate data access and information exchange across multiple data sources, such as payers, financial institutions, Electronic Medical Record (EMR) systems, practice management systems, claims/prescription databases, pharmaceutical companies, physician/hospital portals, pharmacy benefit management (PBM), etc. Further, certain embodiments provide rules based pushing/pulling of information to/from a patient, members of the patient's care team (professional and family), other third parties and specific devices based on profile of each data source. Information can include secure messaging and images and/or scanned clinical documents, for example. Rules can include manual or automatic data exchange, request and acceptance of types of data, etc.

Certain examples provide Web portal applications for data presentation to patients. A Web-based portal can provide an adaptive and proactive experience for users including matching technology/tools, education/information, and guided feedback based upon a patient's specific personality and lifestyle assessment, for example.

Certain examples apply artificial intelligence to compliance tools to form a personalized care plan combined with customized algorithms based on a broad but targeted data set (e.g., patient entered data, EMR data, other third party clinical and financial/administrative data, etc.) to provide tracking of a care management plan, text and graphical projected simulations of an impact to a patient based upon the patient's choices (e.g., your blood pressure will be x vs. y if you do A, B, and C), etc. Projected simulations can include financial as well as medical scenarios, for example.

Certain examples incorporate non-healthcare specific technologies, such as Sametime/synchronous eVisit collaboration tools, social interaction/community sites, tools to help manage healthcare choices (e.g., financial calculators, quality assessment tools, etc.), and the like.

Certain examples facilitate tracking of patient outcomes versus compliance via Medical Quality Improvement Consortium (MQIC) and other infrastructure tools, for example. Certain examples provide an extension of the tools/information exchange architecture for physician specific portal services.

Certain examples provide systems and methods with an ability to aggregate a patient's health information across multiple sources of data (e.g., a physician's electronic medical record, clinic or hospital electronic medical record, payer claims history, pharmaceutical chronic disease management, financial institutions/accounts, etc.) and do so using clinical healthcare information exchange (HIE) standards, for example. Certain examples provide systems connected to a patient's medical record(s) in an interactive way, wherein records automatically adapt to the patient's preferences to achieve the most likely compliance level and/or keep up with changing health conditions of the patient, for example.

Additionally certain examples help address the complex problem of facilitating patient comprehension and decision making by providing standards based organizational tools that automatically adapt to the specific and changing health conditions of the patient and provide comprehensive education and compliance tools to drive positive health outcomes.

Standards-based components are utilized for information exchange. These components can conform to the latest healthcare industry technical standards. In situations where clinical systems that will be sending patient information to participating registries and repositories cannot communicate according to one or more industry standards, messages can be transformed into messages complying with one or more applicable standards prior to being added to the registries or repositories.

Data can be aggregated across multiple data sources to give a patient a global view or a longitudinal record. In prior systems, only a localized view of the patient's information was available via an EMR, insurance claims database, or payer sponsored portal, for example.

In certain examples, registries and repositories are flexible enough to accommodate clinical, financial and demographic data about a patient. Registries and repositories can manage and maintain the data for the life of the patient. In prior systems, the data is no longer available to the patient when the patient is no longer being seen or is managed by another entity (e.g., clinic, payer, and employer). Additionally, a patient can add his or her own information to the registries and repositories. This allows the patient to save personal information about his or her health in a personal health record (PHR).

Certain examples allow the patient to communicate with providers of care by forwarding clinical documents to providers for referral work. Certain examples also enable review of patient created documents by the provider. Certain examples allow the patient to grant or deny access to their information to providers of care. This helps to give the patient more flexibility and better control over his or her record than patients had in prior systems.

Interconnection of multiple data sources helps enable an engagement of all relevant members of a patient's care team and helps improve an administrative and management burden on the patient for managing his or her care. Particularly, interconnecting the patient's electronic medical record and/or other medical data can help improve patient care and management of patient information. Furthermore, patient care compliance is facilitated by providing tools that automatically adapt to the specific and changing health conditions of the patient and provide comprehensive education and compliance tools to drive positive health outcomes.

A healthcare information technology infrastructure can be adapted to service multiple business interests while providing clinical information and services. Such an infrastructure can include a centralized capability including, for example, a data repository, reporting, discreet data exchange/connectivity, "smart" algorithms, personalization/consumer decision support, etc. This centralized capability provides information and functionality to a plurality of users including 1) PHR, devices, and consumer, employer, and physician portals 120; 2) EMR, pay for performance (P4P), chronic disease models, and clinical HIE/RHIO; 3) enterprise pharmaceutical studies; and/or 4) home health including home assurance and home device connectivity, for example.

FIG. 1 illustrates an example healthcare information exchange (HIE) 100. The HIE 100 is organized to provide storage, access and searchability of healthcare information across a plurality of organizations. The HIE 100 may service a community, a region, a nation, a group of related healthcare institutions, etc. For example, the HIE 100 may be implemented as and/or implemented with a regional health information organization (RHIO), national health information network (NHIN), medical quality improvement consortium (MQIC), etc. In certain embodiments, the HIE 100 connects healthcare information systems, practice management systems, and clinical systems, and helps make them interoperable in a secure, sustainable, and standards-based manner.

The HIE 100 provides a capability to exchange information between both related and disparate healthcare information systems. The HIE 100 helps facilitate access to and retrieval of clinical and other healthcare data with improved safety, timeliness and/or efficiency, etc. Components and/or participants in the HIE 100 adhere to a common set of principles and standards for information sharing within a provided technical infrastructure, for example. The HIE 100 may be used to store, access and/or retrieve a variety of data, including data related to outpatient and/or inpatient visits, laboratory results data, emergency department visit data, medications, allergies, pathology results data, enrollment and/or eligibility data, disease and/or chronic care management data/services, etc.

In certain embodiments, the HIE 100 provides a centralized data architecture. However, in certain embodiments, the HIE 100 may also utilize a combined centralized yet partially distributed data architecture. Certain embodiments create an aggregated, patient-centric view of health information. In certain embodiments, the HIE 100 provides one or more large databases of de-identified population data for quality improvement, care management, research, etc. Through the HIE 100, a patient and/or provider may control information access, privacy, and security, for example.

The HIE 100 includes an XDS repository and registry 110, one or more clinical systems 120, one or more lab or radiology systems 130, one or more practice systems 140, claims history 150, and a personal health record (PHR) portal 160. Systems 120, 130, 140 may include a variety of informational and/or query sources, such as healthcare facilities, labs, electronic medical record (EMR) systems, healthcare information systems, insurance systems, pharmaceutical systems, etc. A lab system may include information regarding tests performed on a patient and the results of the tests, for example. A clinical information system may include various types of clinical information regarding a patient, for example. A pharmaceutical system may include information regarding the prescriptions or drugs a patient may be using, for example. Claims history 150 may include records of insurers, for example. The PHR portal 160 may include one or more web viewers or portals, EMR systems, application service provider (ASP) systems, healthcare information systems, practice management systems, etc. Sources 120-160 are examples and other sources may be used. The components of the HIE 100 may be implemented individually and/or in various combinations in software, hardware and/or firmware, for example.

In certain embodiments, the HIE 100 provides a technical architecture, web applications, a data repository including EMR capability and a population-based clinical quality reporting system, for example. The architecture includes components for document storage, querying, and connectivity, such as the XDS registry and repository 110 and claims history 150. The portal 160 may include web portal applications for data presentation to physicians and patients, for example. In certain embodiments, the XDS registry and repository 110 may include an option for a subscription-based EMR for physicians, for example. In certain embodiments, the HIE 100 provides a population-based clinical quality improvement and research database with reporting tools, for example.

In certain embodiments, the XDS registry and repository 110 is a database or other data store adapted to store patient medical record data and associated audit logs in encrypted form, accessible to a patient as well as authorized medical clinics. In an embodiment, the XDS registry and repository 110 can be implemented as a server or a group of servers. The XDS registry and repository 110 can also be one server or group of servers that is connected to other servers or groups of servers at separate physical locations. The XDS registry and repository 110 can represent single units, separate units, or groups of units in separate forms and may be implemented in hardware and/or in software. The XDS registry and repository 110 can receive medical information from a plurality of sources.

Using an XDS standard, for example, in the HIE 100, document querying and storage can be integrated for more efficient and uniform information exchange. Using the HIE 100, quality reporting and research may be integrated in and/or with an RHIO and/or other environment. The HIE 100 can provide a single-vendor integrated system that can integrate and adapt to other standards-based systems, for example.

In certain embodiments, the HIE 100 helps to facilitate the implementation of an MQIC. Via the HIE 100, a group of EMR users may agree to pool data at the XDS registry and repository 110. The HIE 100 may then provide the group with access to aggregated data for research, best practices for patient diagnosis and treatment, quality improvement tools, etc. Through the MQIC and the HIE 100, users may help to improve the quality of healthcare through updated tools and expanded EMR quality improvement reports, for example. The MQIC and the HIE 100 offer members updated clinical information regarding patient illnesses, such as diabetes, heart attack, stroke, hypertension, congestive heart failure, and the like. Data exchange may also be used for clinical research. In certain embodiments, user may opt in or out of particular projects/collaborations via the HIE 100. In certain embodiments, a secure Internet line and/or Web-based portal may be used to access the HIE 100 to participate in a MQIC.

XDS provides registration, distribution, and access across healthcare enterprises to clinical documents forming a patient EMR. XDS provides support for storage, indexing, and query/retrieval of patient documents via a scalable architecture. Prior XDS registries and repositories were defined under IHE to support only one affinity domain, defined as a group of healthcare enterprise systems that have agreed upon policies to share their medical content with each other via a common set of policies and a single registry. Certain examples, however, support multiple affinity domains such that each affinity domain retains its autonomy as a separate affinity domain but shares one instance of hardware and software with the other involved affinity domains. The XDS registry and repository 110 can maintain an affinity domain relationship table used to describe clinical systems participating in each affinity domain. Once a request for a document is made, the source of the request is known and is used to determine which document(s) in the repository 110 are exposed to the requesting user, thus maintaining the autonomy of the affinity domain.

In certain examples, the XDS registry and repository 110 represents a central database for storing encrypted update-transactions for patient medical records, including usage history. In an example, the XDS registry and repository 110 also stores patient medical records. The XDS registry and repository 110 stores and controls access to encrypted information. In an example, medical records can be stored without using logic structures specific to medical records. In such a manner the XDS registry and repository 110 is not searchable. For example, a patient's data can be encrypted with a unique patient-owned key at the source of the data. The data is then uploaded to the XDS registry and repository 110. The patient's data may be downloaded to, for example, a computer unit and decrypted locally with the encryption key. In an example, accessing software, for example software used by the patient and software used by the medical clinic performs the encryption/decryption.

In certain examples, the XDS registry and repository 110 maintains a registration of patients and a registration of medical clinics. Medical clinics may be registered in the XDS registry and repository 110 with name, address, and other identifying information. The medical clinics are issued an electronic key that is associated with a certificate. The medical clinics are also granted a security category. The security category is typically based on clinic type. In certain examples, the requests and data sent from medical clinics are digitally signed with the clinic's certificate and authenticated by the XDS registry and repository 110. Patients may be registered in the XDS registry and repository 410 with a patient identifier and password hash. Patients may also be registered in the XDS registry and repository 110 with name, address, and other identifying information. Typically, registered patients are issued a token containing a unique patient identifier and encryption key. The token may be, for example, a magnetic card, a fob card, or some other equipment that may be used to identify the patient. A patient may access the XDS registry and repository 110 utilizing their token, and in an example, a user identifier and password.

In certain examples, the XDS registry and repository 110 can include program code, such as code implementing an acquisition algorithm, for acquiring data. The acquisition algorithm can acquire data regarding a patient from one or more sources, for example. The acquisition algorithm can acquire information from any of the sources 120-160, for example. The information acquired can be used to update a patient's medical record at the XDS registry and repository 110. In certain examples, the XDS registry and repository 110 also includes program code to perform a normalization algorithm. The normalization algorithm can process the information acquired by the acquisition algorithm and normalize the format. In certain examples, XDS registry and repository 110 can normalize the data acquired from the sources 120-160 into a standard format. The normalized data is stored in the patient's medical record with the XDS registry and repository 110, for example. Alternatively or in addition, one or more of the sources 120-160 can send data to the XDS registry and repository 110 once data is acquired. One or more of the sources 120-160 may have the patient register at the source of the data, for example. One or more of the sources 120-160 may then encrypt the data using the patient identifier and patient encryption key and send the data to the XDS registry and repository 110 to update the patient's medical record. Also, the data may be normalized by the sources 120-160 prior to sending to the XDS registry and repository 110.

For example, the XDS registry and repository 110 may acquire information from a plurality of sources such as 120, 130, and 140. The XDS registry and repository 110 can normalize the acquired data to a standard format. The algorithm unit may receive as input data that is stored at the XDS registry and repository 110 for a patient. The data stored at the XDS registry and repository 110 can be a compilation of data from various sources, such as from payers, financial institutions, electronic medical records, practice management systems, claims databases, pharmaceutical companies, laboratories, physicians, hospitals, and/or other sources. In an example, the patient's report is uploaded to the XDS registry and repository 110 and become part of the patient's medical records.

Figure 2:
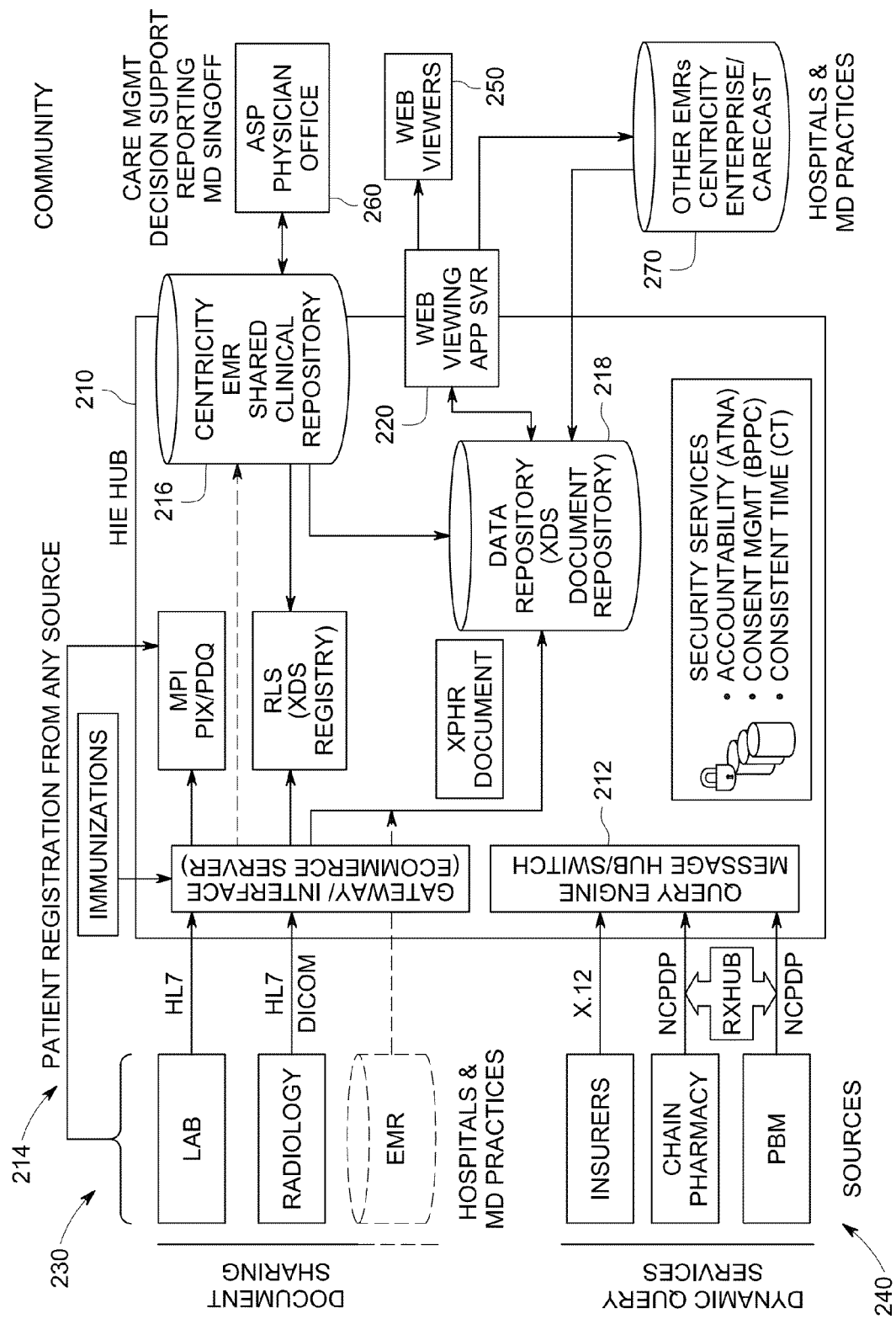
FIG. 2 illustrates an example health information architecture.

FIG. 2 illustrates an example health information architecture 200. The architecture 200 includes an HIE hub 510, one or more data sharing sources 230, one or more data query sources 240, one or more Web viewers 250, a physician office application service provider (ASP) 260 and one or more EMRs 270. The HIE hub 210 may include a plurality of subcomponents, such as a query engine 212, a gateway or interface 214, an EMR shared clinical repository 216, a data repository 218 and a Web viewing application server 220. The hub 210 may also provide security services for the storage, retrieval and query of data, for example. Data source(s) 230 may include EMR, radiology, laboratory and/or other clinical data sources, for example. Data query source(s) 240 may include insurers, pharmacies, prescription benefit managers, and/or other services, for example. The components of the health information architecture 200 may be implemented individually and/or in various combinations in software, hardware and/or firmware, for example.

In operation, document sharing may be facilitated by the architecture 200 via the hub 210. Patient data is passed from one or more sources 220 using an interface standard, such as the standards approved by the Health Information Technology Standards Panel (HITSP) and accepted by the US Department of Health and Human Services (HHS), Health Level Seven (HL7) and/or Digital Imaging and Communications in Medicine (DICOM) communication interface and file format standards. Data enters the hub 210 via the gateway/interface 214. Within the hub 210, a Master Patient Index (MPI), including a patient identifier cross-reference (PIX) and/or a patient demographic query (PDQ) may help facilitate exchanging of relevant patient data. Furthermore, a record locator service (RLS) may be used in the hub 210 to help locate appropriate shared documents using a cross-enterprise document sharing (XDS) registry, for example. Clinical data, documents, and/or images may be stored in the EMR shared clinical repository 216, the data repository 218 and/or source systems such as Radiology/Lab 230.

One or more query sources 240 may transmit query information to the query engine 212 using an interface standard, such as the X.12 and/or National Council for Prescription Drug Programs (NCPDP) communication standard or standards approved by HITSP and accepted by HHS. The query engine 212 serves as a message hub and/or switch to route query messages to appropriate repository(ies).

In certain examples, the data repository 218 includes an XDS document repository populated at least in part by Continuity of Care Documents (CCD) or other clinical summary documents from the Electronic Medical Record (EMR), from any source 230 or 240, or by personal health record (PHR) documents. These documents can be forwarded to users 260 and/or 270, or queried by them. For example, the data repository 218 may include exchanging personal health record (XPHR) content providing common information requested by healthcare providers. Through XPHR, patients may provide a summary of their PHR information to providers, and providers may suggest updates to a patient's PHR after a healthcare encounter.

A community of one or more physician or other healthcare office systems may store, access, or exchange information in the EMR shared clinical repository 216, such as an ASP-based office system 260. For example, information relating to care management, decision support, reporting and/or physician signoff may be utilized. Alternatively and/or in addition, data from the data repository 218 may be exchanged with one or more EMRs 270 (e.g., primary care provider EMRs), for example. Data from the data repository 218 may also and/or alternatively be provided to one or more Web viewers or portals 250 via a Web server or application 220.

In certain examples, a Web portal may be used to facilitate access to information, patient care and/or practice management, for example. Information and/or functionality available via the Web portal may include one or more of order entry, laboratory test results review system, patient information, clinical decision support, medication management, scheduling, electronic mail and/or messaging, medical resources, etc.

In certain examples, the Web portal serves as a central interface to access information and applications, for example. Data may be viewed through the Web-based portal or viewer, for example. Additionally, data may be manipulated and propagated using the Web portal, for example. Data may be generated, modified, stored and/or used and then communicated to another application or system to be modified, stored and/or used, for example, via the Web portal and HIE hub.

The Web portal may be accessible locally (e.g., in an office) and/or remotely (e.g., via the Internet and/or other private network or connection), for example. The Web portal may be configured to help or guide a user in accessing data and/or functions to facilitate patient care and practice management, for example. In certain examples, the Web portal may be configured according to certain rules, preferences and/or functions, for example. For example, a user may customize the Web portal according to particular desires, preferences and/or requirements.

In certain examples, an XDS profile and/or protocol (e.g., an Integrating the Healthcare Enterprise Cross-Enterprise Sharing of Medical Summaries Integration Profile (IHE XDS-MS) protocol) may be used to define a coupling or connection between one or more entities for patient document sharing. For example, XDS may be used to form a query identifying sources with information about a particular patient and/or other criteria, determining an identifier used to associate clinical data related to the patient and/or other criteria and request patient information from the appropriate source and/or repository, such as an XDS document repository 518, for example. As discussed above, a record locator service (RLS) may also be used to facilitate sharing of information between organizations.

In certain examples, the hub 210 provides security services during transmission and querying of data. Security services may include generation and storage of audit records, such as audit trail and node authentication (ATNA) accountability records. Additionally, security services may include patient privacy consent management, such as basic patient privacy consent (BPPC). Security services may also include coordination or consistency of time (CT) across network systems.

In certain examples, the architecture 200 supports trusted intermediaries or actors within the hub 210 to associate identity and trust among data/service providers and data/service clients. Once a source and/or user have been authenticated, the hub 210 can use the authentication to establish a security context for the data. Patient privacy consent, such as BPPC may provide a profile for access control to data and/or systems, for example. Patient consent is obtained from a patient and establishes rules for sharing and using patient data. Patient privacy consent may combine with authentication, for example, to help ensure reliability and security in the architecture 200. For example, cross-user authentication and patient consent may be used to authenticate sharing of EMR information for a patient between two healthcare entities. A BPPC profile may provide an implementation of privacy consent policies in the architecture 200, and a language or protocol, such as Extensible Access Control Markup Language (XACML), may be used with the BPPC to implement access control rules.

Using one or more of the systems described above, an end-to-end digital health services and platform can be provided to help enable a personalized, adaptive, and more comprehensive patient medical record that is connected with the patient's physicians/care team, payers, employers, and financial institutions. Medical records can be aggregated and connected via an XDS registry and repository and shared by multiple sources/users of data as well as services. For example, information from a physician's electronic medical record for a patient, a clinic or hospital electronic medical record, payer claims history, pharmaceutical chronic disease management, and/or financial institutions/accounts can be interactively aggregated using clinical HIE standards. Such interconnection helps personal health records automatically adapt to a patient's preferences to achieve a most likely compliance level and/or keep up with changing health conditions of a patient, for example. Additionally, patient comprehension and decision making can be facilitated by providing standards-based organizational tools that automatically adapt to the specific and changing health conditions of the patient and provide more comprehensive educational and compliance tools to help drive positive health outcomes.

Certain examples enable documentation and measurement of improvement across multiple therapeutic and wellness areas. Certain examples provide delivery and quality of recommended care along with patient compliance and outcomes management. For example, using an enterprise model as described above, adoption of disease state protocols for a variety of target audiences, locations, and methodologies leads to measurable, meaningful, and scalable outcomes. Via an access portal, such as a Web-based access portal, a user, such as a patient, clinician, or payer, can access information and educational services at a point of care and/or outside a visit as well as generate measured outcomes.

Certain examples provide clinician-directed intervention with a patient through an EMR platform including incorporating treatment and disease management guidelines into an EMR, providing professional education and training such as general disease overview and patient case-based information, and offering customized patient education electronically via the EMR, for example. Outcomes can be measured and managed via the EMR/MQIC and access portal in an enterprise model, for example.

Figure 3:
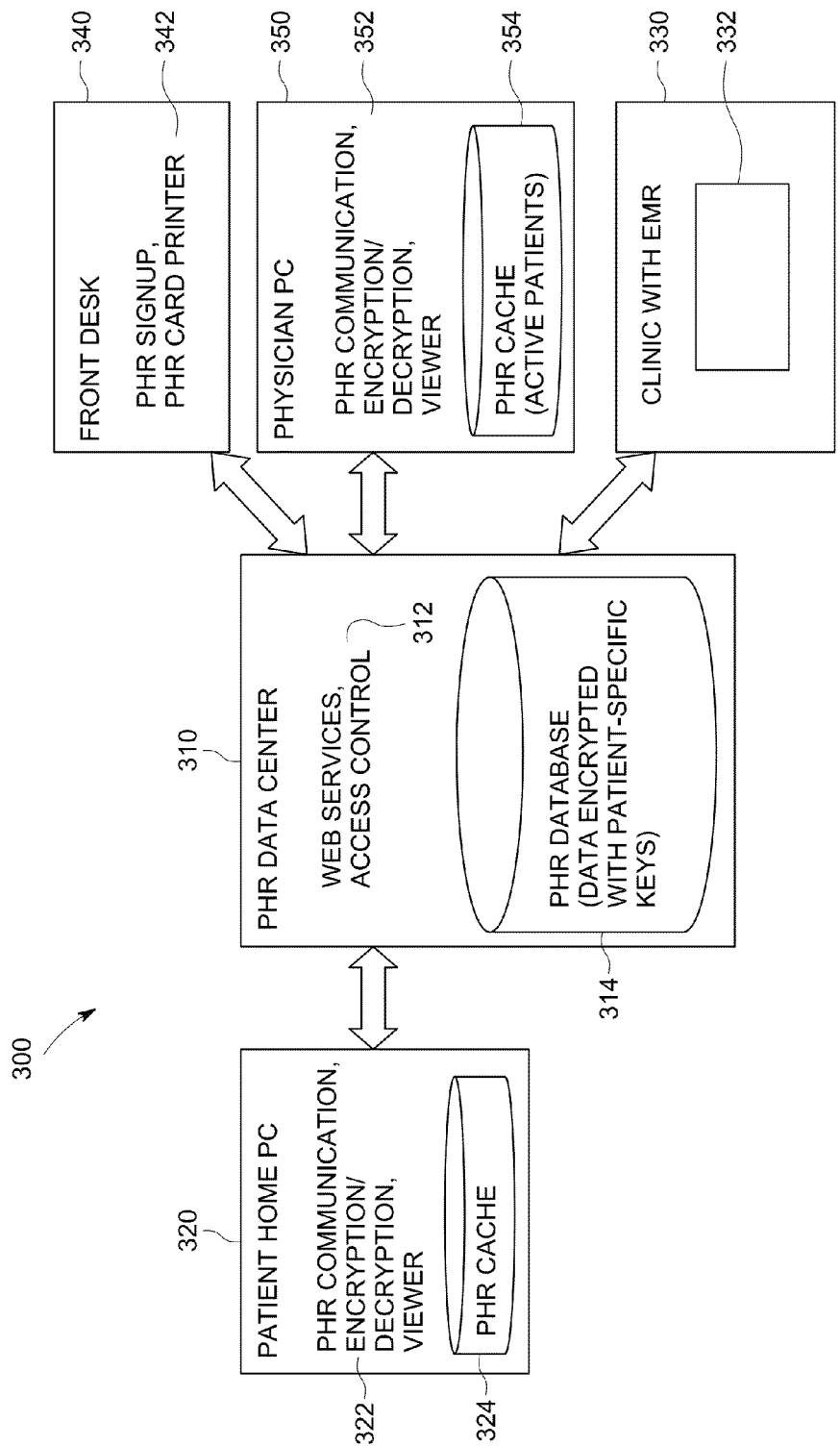
FIG. 3 illustrates an example personal health record (PHR) system.

In addition to clinic PHR/EMR systems and methods, information and access can be provided via a local user computer with access to a remote server (e.g., a remote PHR server). FIG. 3 illustrates an example PHR system 300 controlled by an individual to manage clinical information for the individual at a physician office. The system 300 includes a data center 310, a patient home computer 320, a clinic server 330, a front desk or reception interface 340, and a physician computer 350.

In an example, the data center 310 includes a PHR database and/or other data store 314 for storing patient medical record data and associated audit logs in encrypted form, accessible to the patient as well as authorized care provider organizations (including hospitals, doctor's offices, and/or other diagnosis/treatment facilities). In an example, the data center 310 can be a server or a group of servers and/or reside on a server or group of servers, for example. The data center 310 can also be one server or group of servers that is connected to other servers or groups of servers at separate physical locations. The data center 310 can represent single units, separate units, or groups of units in separate forms and can be implemented in hardware and/or in software. In an example, the data center 310 receives medical information from a plurality of sources. For example, the sources of clinical information can include various clinics, labs, pharmacies, as well as the patient him/herself.

The data center 310 also includes Web services 312 to provide access control and interface capability between the patient computer 320, the clinic server 330, the front desk interface 340, the physician computer 350, and the PHR database 314. Requests to store and/or retrieve data via the database 314 are routed through and approved by the data center Web services 312 according to one or more rules, preferences, and/or user profiles, for example.

In an example, the database 314 of the data center 310 represents a central database 314 for storing encrypted update-transactions for patient medical records, including usage history. In an example, the database 314 also stores the patient medical records. The data center 310 stores and controls access to encrypted information. In an example, medical records can be stored without using logic structures specific to medical records. In such a manner the database 314 is not searchable. For example, a patient's data can be encrypted with a unique patient-owned key at the source of the data. The data is then uploaded to the data center 310. The data center 310 does not process or store unencrypted data thus minimizing privacy concerns. The patient's data can be downloaded to, for example, a computer and decrypted locally with the encryption key. In an example, accessing software, for example software used by the patient and software used by the medical clinic performs the encryption/decryption.

For example, the database 314 can be structured according to clinic, patient, patient/clinic association, and document. Clinic information can include, for example, an identifier, a name, and address, a public key, and one or more security categories. Patient information can include, for example, an identifier, a password hash, and an encrypted email address. Patient/clinic association information can include a clinic identifier, a patient identifier, an encrypted key, and one or more override security categories. Document information can include an identifier, a patient identifier, a clinic identifier, a security category, and encrypted data, for example.

The data center 310 can maintain a registration of patients and a registration of medical clinics. Medical clinics can be registered in the data center 310 with name, address, and other identifying information. The medical clinics are issued an electronic key that is associated with a certificate. The medical clinics are also granted a security category. The security category is typically based on clinic type. In an example, the requests and data sent from medical clinics are digitally signed with the clinic's certificate and authenticated by the data center 310. Patients can be registered in the data center 310 with a patient identifier and password hash, without any identifying information. Typically, registered patients are issued a token containing a unique patient identifier and encryption key. The token can be, for example, a paper card, a magnetic card, a fob card, or some other equipment that can be used to identify the patient. A patient can access the data center 310 utilizing their token, and in an example, a user identifier and password.

As discussed above, the data center 310 is in communication, via the Web services 312, with the patient computer 320, the clinical server 330, the reception interface 340, and the physician computer 350. The data center 310, patient computer 320, clinical server 330, reception interface 340, and physician computer 350 can be in communication via any computer hardware, firmware, and/or software that can process electronic communications to/from the data center 310, patient computer 320, clinical server 330, reception interface 340, and physician computer 350.

A user can download a medical record from the data center 310, decrypt the medical record via the patient computer 320, such as a personal or handheld computer, and then process the data on a local basis, for example. For example, a viewer 322 at the patient computer 320 can be used for PHR communication, data encryption/decryption, and viewing. The viewer 322 can facilitate download of PHR data for the patient from the data center database 314 and storage of the patient data in a PHR cache 324 at the patient computer 320, for example.

Similarly, the physician computer 340 can be used to download medical record information from the data center 310. For example, medical record information can be stored in the PHR database 314 and be accessible by the physician computer 340 via the Web services 312. As another example, medical record information can be stored at the data center 310 from the clinic EMR 332 via the clinical server 330.

In certain examples, one or more of the patient computer 320, clinic server 330, front desk interface 340, and/or physician computer 350 can be used to send data to the data center 310 for medical record update. For example, a receptionist and/or patient at the front desk interface 340 can access the PHR data center 310 for PHR signup, check-in, and/or identification generation, such as via the PHR card printer 342. As another example, a user at the physician computer 350 can access the PHR data center 310 via a viewer 352 that facilitates PHR communication, encryption/description, and display of PHR data. The viewer 352 can be used to retrieve PHR data from the database 314 for storage in a PHR cache 354 of active patients for the physician, for example.

Alternatively and/or in addition, sources such as laboratory results, pharmaceutical information, patient examination information, and image acquisitions, can provide data for storage at the data center 310. In certain examples, a patient and/or authorized clinician can register or log in using a patient and/or clinician identifier, certificate, etc. Data can then be encrypted using the identifier and an encryption key and sent to the data center 310 to update a patient's medical record in the database 314. Also, the data can be normalized prior to sending to the data center 310.

In an example, data center 310, patient computer 320, clinic server 330, reception interface 340, and/or physician computer 350 can be connected to one or more of each other via network connections, for example through the Internet or private network.

Figure 4:
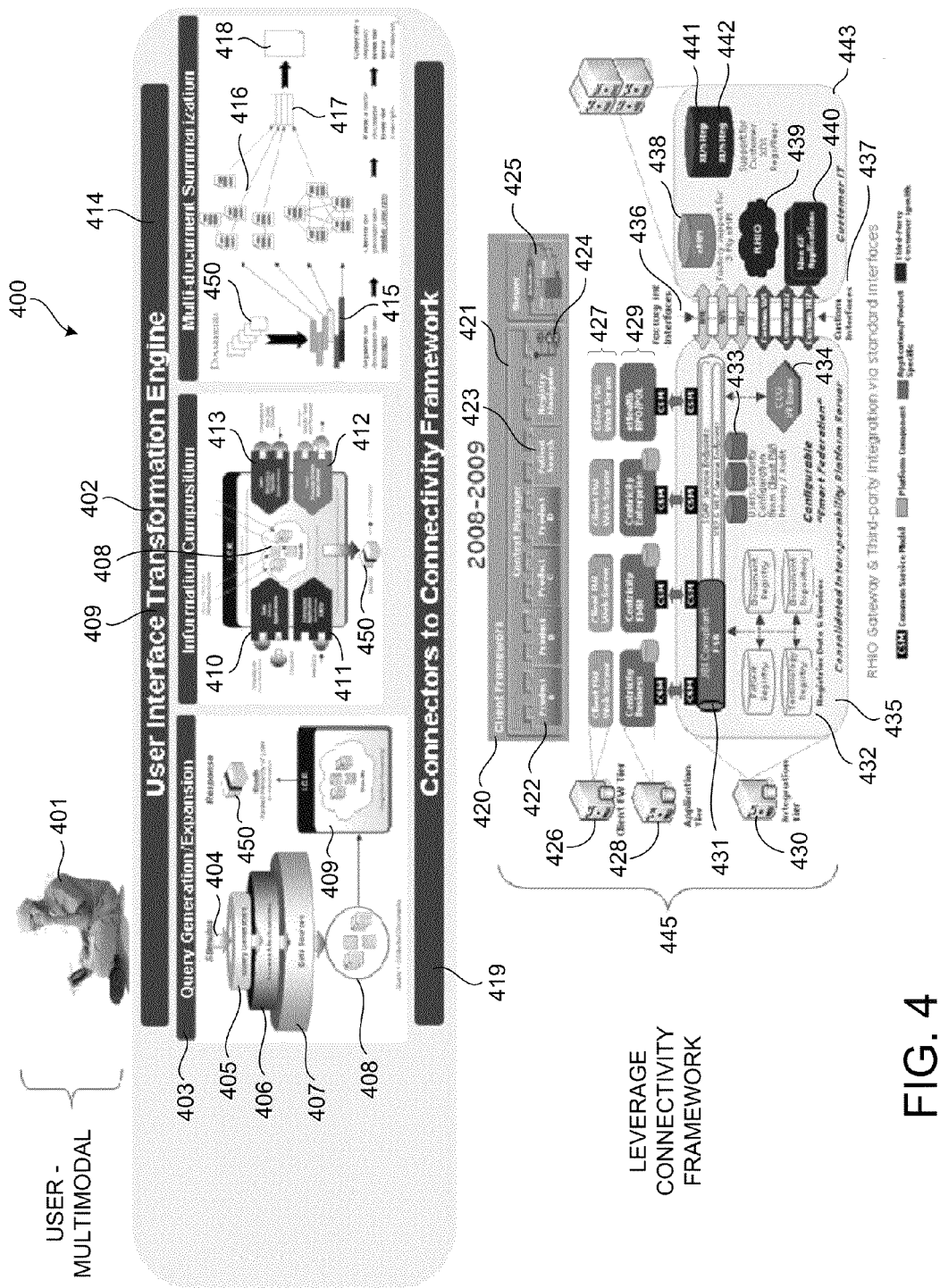
FIG. 4 depicts an example user interface architecture.

FIG. 4 depicts an example user interface architecture 400. The architecture 400 includes a user interface transformation engine 402, a query generation/expansion engine 403, an information composition engine 409, a multi-document summarization engine 414, and one or more connectors 419 to a connectivity framework 445. The components of the architecture 400 are accessible by a user via a user interface 401 on a processing device, such as a computer or handheld device. The user can submit a query for information via the user interface 401, for example.

The query generation/expansion engine 403 includes a stimulus 404, one or more query generators 405, and one or more access mechanisms 406 to search one or more data source 407 to produce a query and collected documents 408. The query and collected documents 408 are passed to the information composition engine 409 that includes applications 410, 411, 412, 413 that process and apply cognitive reasoning, for example, to organize the query and collected documents 408 into one or more units meaningful to a requesting user based on one or more of semantic guidelines, user preferences, and domain-related information, for example. A toolset including composers can employ Composition Decision Logic (CDL), such as aggregation, elimination of redundant information, lightweight summarization of information, and fusion of results, to compose the information. Applications can include one or more data driven applications 410, enterprise application interfaces 411, task/process driven applications 412, and data structure specific applications 413, for example. The applications 410, 411, 412, and/or 413 can include one or more templates related to new data types, new data structures, domain specific tasks/processes, new application interfaces, etc. Composition and processing of the query and collected documents 408 produces a bundle 410 of information in response to a user query.

The multi-document summarization engine 414 receives the bundle 410 of documents and segments the documents into passages 415. The passages 415 are clustered based on similar concepts 416. A meta-document 417 is then formed from the concepts 416. A summary 418 is generated from the meta-document 417. Query results 410, the meta-document 417, and/or the meta-document summary 418 can be provided to the user via the user interface 401.

Via connectors 419 to a connectivity framework 445, the user interface 401 and its engines 403, 409, 414 can send and receive information in response to user query via the interface 401, for example. For example, the query engine 403 can access the connectivity framework 445 to query one or more data sources 407.

The connectivity framework 445 includes a client framework 420. The client framework 420 includes a context manager 421 for one or more products 422, a patient search 423, a registry navigator 424, and a viewer 425. Thus, in certain embodiments, the connectivity framework 420 can facilitate viewing and access to information via the user interface 401 and apart from the user interface 401. Via the connectivity framework 445, the query engine 403 and/or other parts of the user interface 401 can access information and/or services through a plurality of tiers.

Tiers can include a client framework tier 426, an application tier 428, and an integration tier 430, for example. The client framework tier 426 includes one or more client web servers 427 facilitating input and output of information, for example. The applicant tier 428 includes one or more applications 429 related to enterprise and/or departmental usage such as business applications, electronic medical records, enterprise applications, electronic health portal, etc. The integration tier 430 includes a consolidated interoperability platform server 435 in communication with customer information technology (IT) 443 via one or more factory 436 and/or custom 437 interfaces, such as default and/or customized interfaces using a variety of message formats such as a web service (WS), X12, Health Level Seven (HL7), etc. The consolidated interoperability platform 435 can communicate with the one or more applications 429 in the application tier 428 via a common service model (CSM) and/or generic message model, for example.

As shown, for example, in FIG. 4, the consolidated interoperability platform 435 includes an enterprise service bus (ESB) 431, a collection of registries, data, and services 432, configuration information 433, and a clinical content gateway (CCG) interface engine 434, for example. The ESB 431 can be a Java business intelligence (JBI) compliant ESB, for example. The ESB 431 can include one or more endpoints or locations for accessing a Web service using a particular protocol/data format, such as X12, HL7, SOAP (simple object access protocol), etc., to transmit messages and/or other data, for example. Using a CSM, the ESB 431 facilitates communication with the applications 429 in the application tier 428, for example. Via the ESB 431, information in the registries, data and services repository 432 can be provided to the applicant tier 431 in response to a query, for example. Configuration information 433 can be used to specify one or more parameters such as authorized users, levels of authorization for individual users and/or groups/types of users, security configuration information, privacy settings, audit information, etc. The CCG interface engine 431 receives data from the customer IT framework 443 and provides the data to the registries 432 and/or applications 429 in the application tier 431, for example.

As shown, for example, in FIG. 4, the customer IT 443 includes support for a third party electronic Master Patient Index (eMPI) 438, support for a regional health information organization (RHIO) 439, one or more third party applications 440, support for a cross-enterprise document sharing (XDS) repository 441, support for an XDS registry 442, and the like. Using customer IT 443 in conjunction with the interoperability platform 435, a RHIO gateway and third party application integration can be provided via one or more interfaces to the connectivity framework 445 and/or the query generation/expansion engine 403 of the user interface 401.

The customer IT framework 443 can be organized to provide storage, access and searchability of healthcare information across a plurality of organizations. The customer IT framework 443 may service a community, a region, a nation, a group of related healthcare institutions, etc. For example, the customer IT framework 443 can be implemented with the RHIO 439, a national health information network (NHIN), a medical quality improvement consortium (MQIC), etc. In certain embodiments, the customer IT 443 connects healthcare information systems and helps make them interoperable in a secure, sustainable, and standards-based manner.

In certain embodiments, the customer IT framework 443 provides a technical architecture, web applications, a data repository including EMR capability and a population-based clinical quality reporting system, for example. The architecture includes components for document storage, querying, and connectivity, such as the XDS registry 442 and repository 441. In certain embodiments, the XDS registry 442 and repository 441 can include an option for a subscription-based EMR for physicians, for example. In certain embodiments, the XDS registry 442 and repository 441 are implemented as a database or other data store adapted to store patient medical record data and associated audit logs in encrypted form, accessible to a patient as well as authorized medical clinics. In an embodiment, the XDS registry 442 and repository 441 can be implemented as a server or a group of servers. The XDS registry 442 and repository 441 can also be one server or group of servers that is connected to other servers or groups of servers at separate physical locations. The XDS registry 442 and repository 441 can represent single units, separate units, or groups of units in separate forms and may be implemented in hardware and/or in software. The XDS registry 442 and repository 441 can receive medical information from a plurality of sources.

Using an XDS standard, for example, in the customer IT framework 443, document querying and storage can be integrated for more efficient and uniform information exchange. Using the customer IT 443, quality reporting and research may be integrated in and/or with an RHIO 439 and/or other environment. The customer IT 443 can provide a single-vendor integrated system that can integrate and adapt to other standards-based systems, for example.

Via the customer IT framework 443, a group of EMR users may agree to pool data at the XDS registry 442 and repository 441. The customer IT framework 443 can then provide the group with access to aggregated data for research, best practices for patient diagnosis and treatment, quality improvement tools, etc.

XDS provides registration, distribution, and access across healthcare enterprises to clinical documents forming a patient EMR. XDS provides support for storage, indexing, and query/retrieval of patient documents via a scalable architecture. Certain embodiments, however, support multiple affinity domains (defined as a group of healthcare enterprise systems that have agreed upon policies to share their medical content with each other via a common set of policies and a single registry) such that each affinity domain retains its autonomy as a separate affinity domain but shares one instance of hardware and software with the other involved affinity domains. The XDS registry 442 and repository 441 can maintain an affinity domain relationship table used to describe clinical systems participating in each affinity domain. Once a request for a document is made, the source of the request is known and is used to determine which document(s) in the repository 441 are exposed to the requesting user, thus maintaining the autonomy of the affinity domain.

In certain examples, the XDS registry 442 and repository 441 represent a central database for storing encrypted update-transactions for patient medical records, including usage history. In an example, the XDS registry 442 and repository 441 also store patient medical records. The XDS registry 442 and repository 441 store and control access to encrypted information. In an embodiment, medical records can be stored without using logic structures specific to medical records. In such a manner the XDS registry 442 and repository 441 is not searchable. For example, a patient's data can be encrypted with a unique patient-owned key at the source of the data. The data is then uploaded to the XDS registry 442 and repository 441. The patient's data can be downloaded to, for example, a computer unit and decrypted locally with the encryption key. In an example, accessing software, for example software used by the patient and software used by the medical clinic performs the encryption/decryption.

In certain examples, the XDS registry 442 and repository 441 maintain a registration of patients and a registration of medical clinics. Medical clinics may be registered in the XDS registry 442 and repository 441 with name, address, and other identifying information. The medical clinics are issued an electronic key that is associated with a certificate. The medical clinics are also granted a security category. The security category is typically based on clinic type. In certain examples, the requests and data sent from medical clinics are digitally signed with the clinic's certificate and authenticated by the XDS registry 442 and repository 441. Patients may be registered in the XDS registry 442 and repository 441 with a patient identifier and password hash. Patients may also be registered in the XDS registry 442 and repository 441 with name, address, and other identifying information. Typically, registered patients are issued a token containing a unique patient identifier and encryption key. The token may be, for example, a magnetic card, a fob card, or some other equipment that may be used to identify the patient. A patient may access the XDS registry 442 and repository 441 utilizing their token, and, in an example, a user identifier and password.

Figure 5:
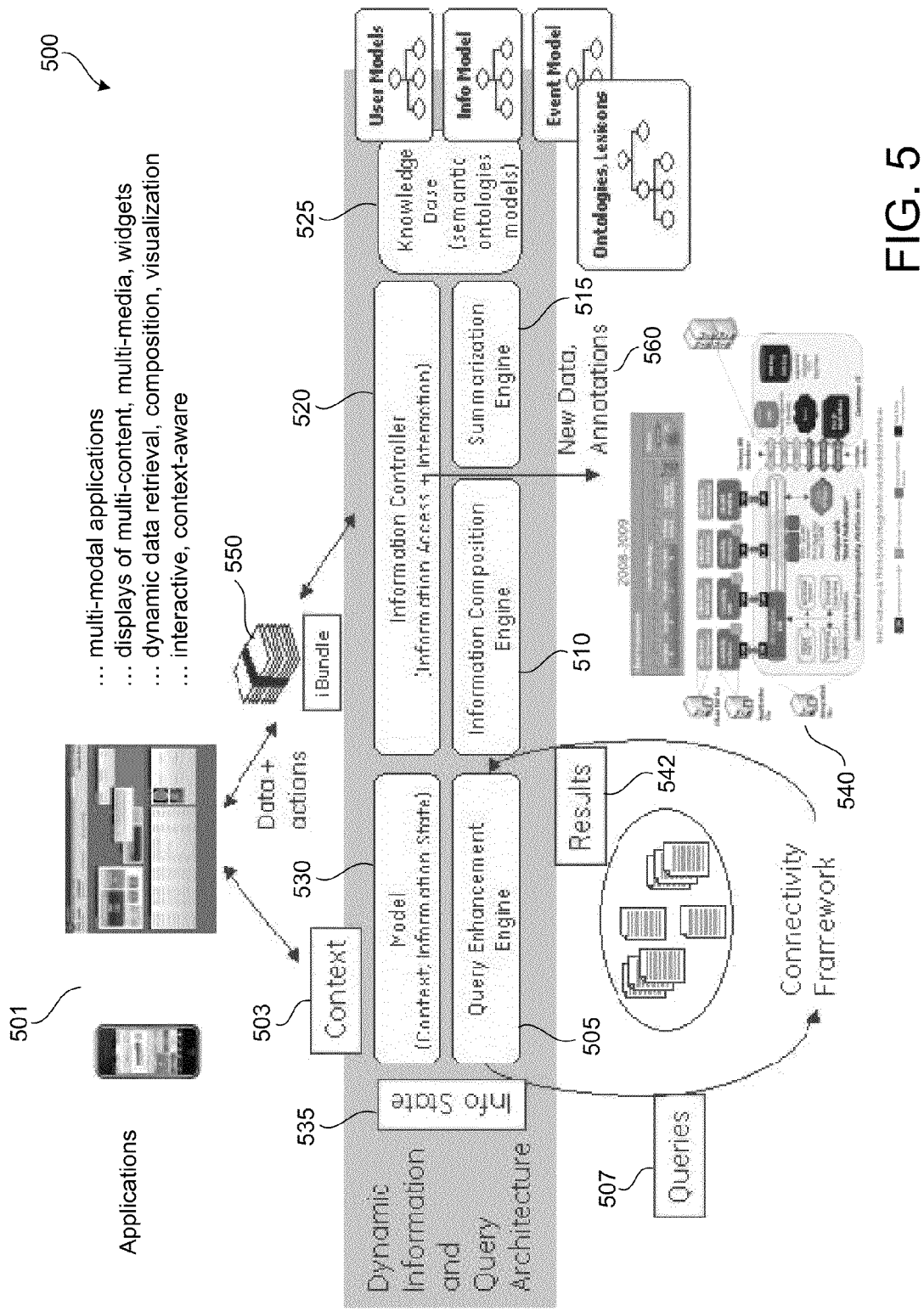
FIG. 5 depicts an example information architecture provided to support retrieval, composition, and presentation of information from multiple, heterogeneous data sources.

As illustrated, for example, in FIG. 5, an information architecture 500 is provided to support retrieval, composition (e.g., bundling), and presentation of information from multiple, heterogeneous data sources. Components of the architecture 500 include a query enhancement engine 505, an information composition engine 510, a summarization engine 515, an information controller 520, a knowledge base 525, a model 530, and an information state 535.

The query enhancement engine 505 generates queries, searches data repositories, and filters results to find relevant information based on a context 503. The information composition engine 510 composes and assembles retrieved information into an information bundle that is organized as relevant to a user. The summarization engine 515 includes single and multi-document summarization engines to provide summaries of content, clustering, and identification of salient themes of retrieved information. The information controller 520 provides structure and interactive access to retrieved information and enables use of diverse visualization strategies to more effectively present invention. The knowledge base 525 provides models (e.g., user models, information models, event models, ontologies, lexicons, etc.) for users, events, and information to enable utilization of semantic relationships.

FIG. 5 illustrates a high-level view of these technologies integrated with a user interface system to improve the retrieval of relevant information, compose the collected information into meaningful information bundles 550, and display the information to the user for a particular context 503. One or more applications 501 for querying and displaying and/or otherwise processing results can be either thick clients that run on a personal computer/workstation or mobile-applications running on a handheld or other mobile device (e.g., a personal digital assistant or cellular phone). These applications 401 can be composed, for example, by assembling multiple information widgets which can display different kinds of data. For example, one widget may be used to display textual information summarizing patient medications, while another widget may enable x-ray (e.g., images) or ultrasound (e.g., video) to be displayed. Other widgets may enable the display of data among different dimensions, such as time, and allow the user to interact with the data to drill-down into more detail, for example.

The information architecture 500 provides mechanisms for applications 501 to retrieve information from disparate data sources and provide that data to applications 501 in a structured way to enable meaningful information display to the user. Information widgets interact with the architecture 500 via the information controller 520. Via the controller 520, the application 501 can provide context 503 about the user (e.g., role and preferences) and the underlying event (e.g., patient stroke workup). The controller 520 can provide this information to the query enhancement engine 505 to identify data sources and retrieve the most relevant information via one or more queries 507 of a connectivity framework 540 to provide results 542. The retrieved information is then examined by the information composition engine 510 for bundling and composition. Some information can be summarized by the summarization engine 515 before the information bundle (or i-bundle) 550 is returned to the application 501 for presentation.

The knowledge base 525 contains models of roles, users, events, and information as well as medical ontologies. These semantic concepts are available to other components, such as the query enhancement engine 505 or the information composition engine 510 to improve the retrieval and bundling of information for the user.

For some applications 501, it may be desirable for the user to enter new data or to annotate the data that has been retrieved. The information controller 520 provides mechanisms for making these data updates. For example, new data and/or other action 555 can be provided from the application 501 to the information controller 520 for future use. Alternatively or in addition, new data and/or annotations 560 can be provided via the information controller 520 to the connectivity framework 540.

Thus, semantic information can be shared and leveraged by components for use in retrieving information based on semantic concepts and relationships, organizing retrieved information based on semantic relationships, and showing relationships among information and data retrieved using semantic concepts and relationships. For example, a longitudinal temporal display of patient information can be improved by enabling the display of various relationships between data that is semantically related. Reasoning mechanisms can be integrated to enable information to be more effectively inserted into a workflow to enable more decision support at a point of patient care. Reasoning engines can be integrated to enable information to be dynamically delivered to users at different points during care of a patient.

Certain examples allow healthcare information systems to find and make use of relevant information across a timeline of patient care. For example, a search-driven, role-based interface allows an end user to access, input, and search medical information seamlessly across a healthcare network. An adaptive user interface provides capabilities through a work-centered interface tailored to individual needs and responsive to changes in a work domain, for example. Semantic technology can be leveraged to model domain concepts, user roles and tasks, and information relationships. The semantic models enable applications to find, organize and present information to users more effectively based on contextual information about the user and task. Components forming a framework for query and result generation include user interface frameworks/components for building applications; server components to enable more efficient retrieval, aggregation, and composition of information based on semantic information and context; and data access mechanisms for connecting to heterogeneous information sources in a distributed environment.

A variety of user interface frameworks and technologies can be used to build applications including, Microsoft® ASP-.NET, Ajax®, Microsoft® Windows Presentation Foundation, Google® Web Toolkit, Microsoft® Silverlight, Adobe®, and others. Applications can be composed from libraries of information widgets to display multi-content and multi-media information, for example. In addition, the framework enables users to tailor layout of the widgets and interact with underlying data.

Healthcare information can be distributed among multiple applications using a variety of database and storage technologies and data formats. To provide a common interface and access to data residing across these applications, a connectivity framework (CF) is provided which leverages common data and service models (CDM and CSM) and service oriented technologies, such as an enterprise service bus (ESB) to provide access to the data.

Figure 6:
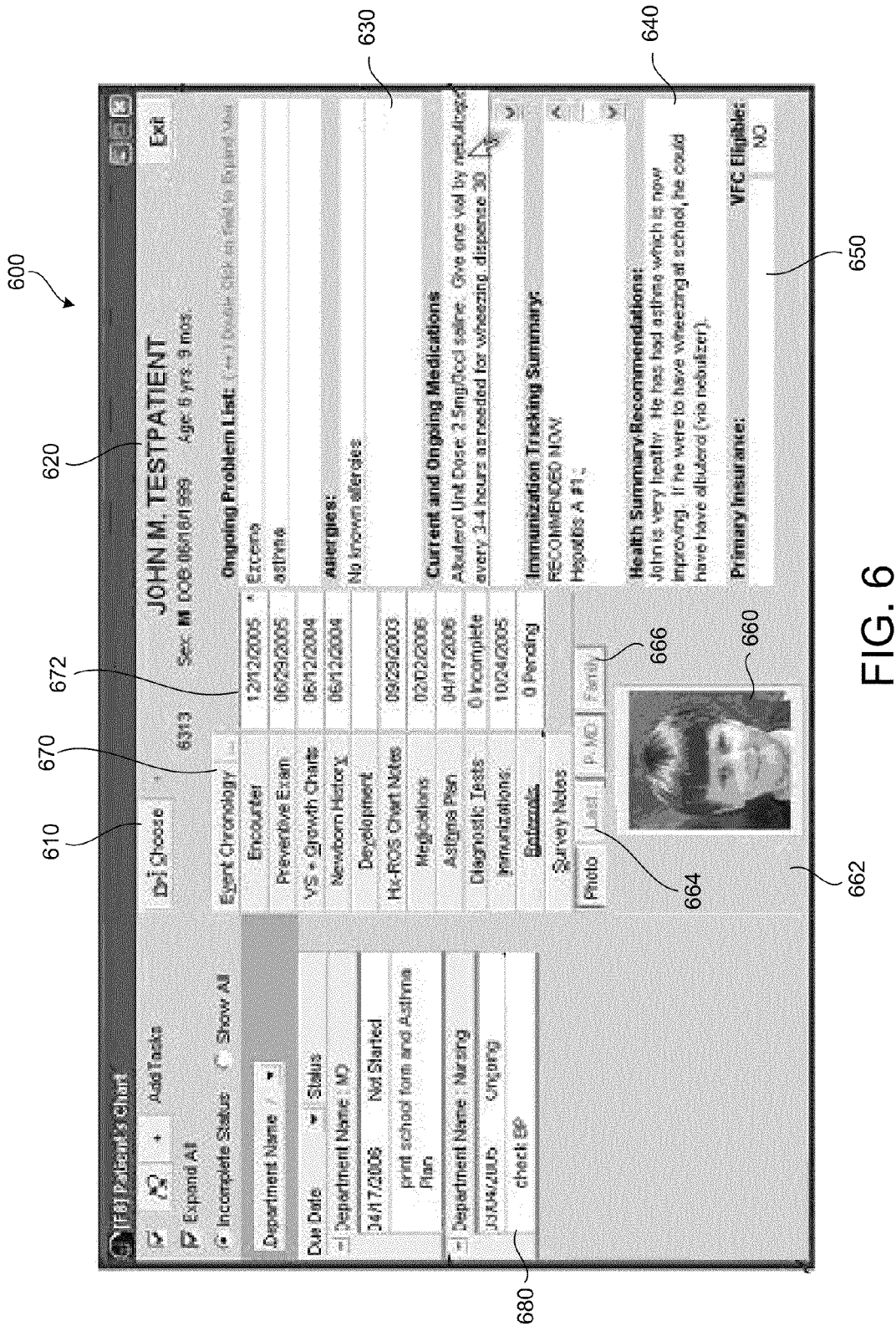
FIG. 6 illustrates an example electronic patient chart.

In certain examples, a healthcare information framework, such as an HIE, EMR, PHR, and/or other clinical information storage system or network can be mined to connect records based on some linking criteria (family, condition, etc.). FIG. 6 illustrates an example electronic patient chart 600. As shown in FIG. 6, the electronic patient chart 600 includes a choose option 610 allows a user to access a patient directory and all available patient charts. Patient identifying information 620, such as name, age, gender, and date of birth, is displayed for review via the chart 600. Patient status information 630, including information such as a list of ongoing problems, allergies, on-going medications, etc., is displayed to notify a provider and bring him or her up to date on the patient's status. Health summary recommendations 640 provide a summary of on-going issues and instructions for medication and care. Recommendations 640 can be as lengthy and detailed as desired. The summary 640 can print and/or otherwise output automatically to school and camp forms, notifying nurses and caregivers of patient issues, for example. Insurance information 650, optionally including additional details such as vaccines for children eligibility, is also displayed.

A picture 660, such as a black and white or color photograph, of the patient can be displayed as part of the chart 600. In some examples, selecting the picture 660 and/or a button 662, such as a plus symbol (+) next to the picture 660 allows the user to view additional pictures of the patient. Additional options such as a "Last" button 664 can provide a summary of the patient's last visit and/or several previous visits, for example. A "Family" button 666 can be used to provide information regarding the patient's family members, such as parents, siblings, etc., and/or other connected individuals. Alternatively or in addition, a "Relationship" button can be used to provide information regarding the patient's entire relationship tree, covering all relationship linkages with other patients.

A column and/or other group of buttons 670 provides access to tools and features in one or more clinical systems accessible via the chart 600. From the chart screen 600, a provider can access functionality such as event chronology, growth charts, medications, notes, plans, tests, etc. Dates 672 corresponding to the tool/feature options 670 inform the provider of the last preventive exam, growth chart, medication, etc., and update the provider with the status of test results and/or referrals, for example.

A checklist 680 provides instructions, reminders, and/or status reports for pending tasks in a clinical environment, such as a hospital, clinic, physician office, etc. The checklist 680 helps enable the provider to delegate tasks in the office to different personnel and track progress, for example.

Figure 7:
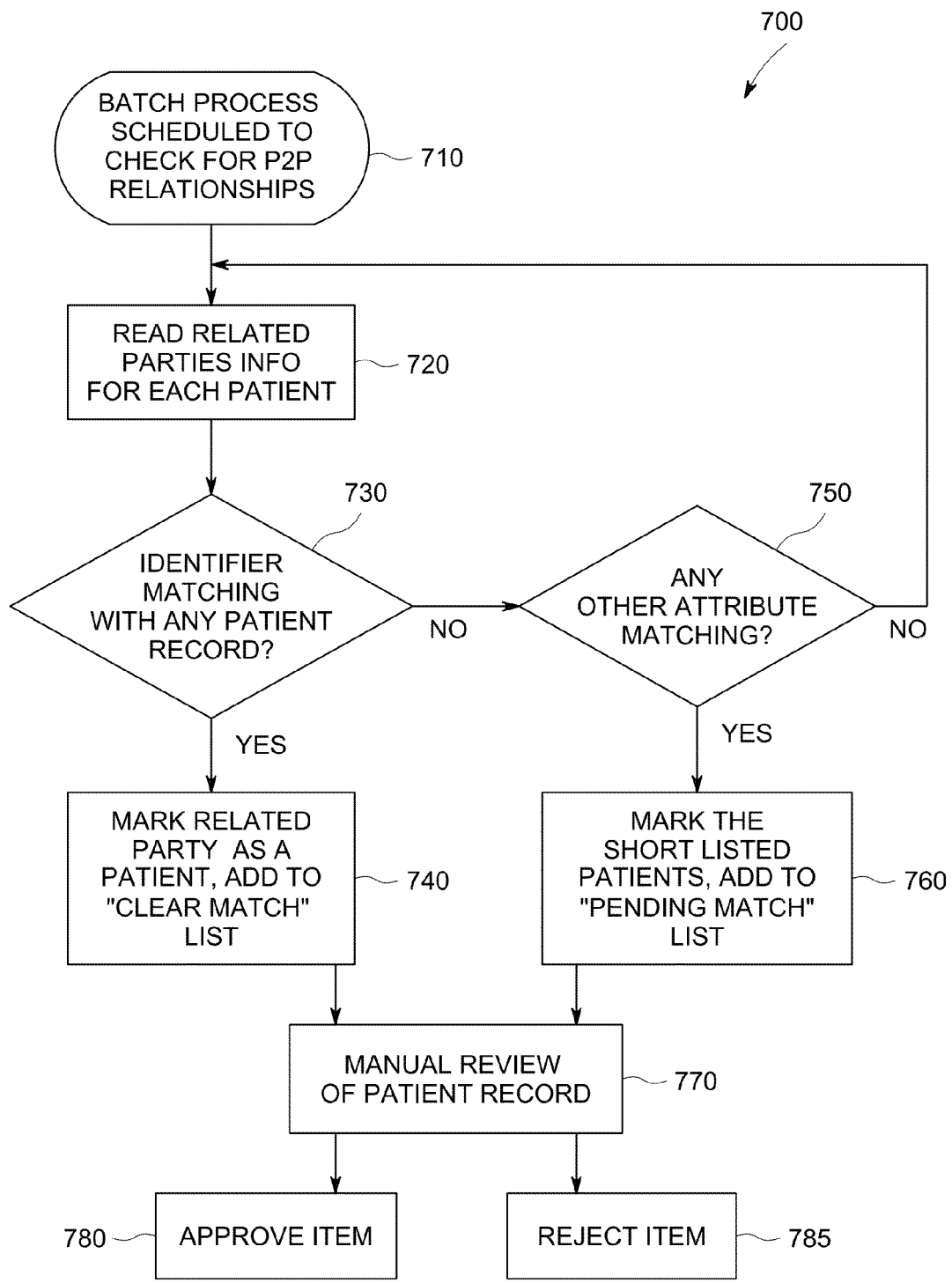
FIG. 7 illustrates a flow diagram for an example method to identify patient-to-patient relationships among electronic medical records and/or other electronic data.

FIG. 7 illustrates a flow diagram for a method 700 to identify patient-to-patient relationships among electronic medical records and/or other electronic data. Aggregation of patient relationship information can be achieved through a linking process involving automated (and possibly manual) steps, for example. At block 710, electronic records (e.g., EMR, EHR, PHR, and/or other electronic patient documents) are processed to identify patient-to-patient relationships. For example, a batch process is scheduled on a computer system, such as an EMR, PACS, RIS, practice management, and/or other computer system, to check for P2P relationships with respect to a particular patient, group of patients, etc. In some examples, an automated linking process runs as a batch process, which periodically scans a patient information data store for "related/dependent/associated party" details matching an existing patient.

At block 720, identifiers provided for a related/dependent/associated party are read and compared against available patient identifiers. The patient identifiers can be any identifier (e.g., a number) and/or combination of attributes that helps to uniquely identify a patient. At block 730, a match between identifiers is determined. If an exact match is obtained, then, at block 740, the patient record is marked against the related party and is added to a "clear match" list. If more than one patient record match is obtained for any of the given identifiers, the patient records are marked against the related party and are added to a "pending match" list.

If the identifier match fails, at block 750, the process looks up other relevant attributes such as phone number, name, address, etc., and/or a combination of attributes to help identify a patient. These attributes can be configured to be included in the patient search. If one or more matches are found for the other attributes, at block 760, the patient record(s) are marked against the related party and are added to the "pending match" list.

In some examples, a manual process, which approves/rejects the matches after scrutiny, follows the automated process. If matching results rankings are made available to the matching algorithm, the rankings can help prioritize the match results and thus aid the manual review and linking process. The matching algorithm can be configured to use one or more identifiers for matching. Example identifiers can include but are not limited to Master Patient Identifier (e.g., a unique identifier issued by a local/community/national authority), Hospital Medical Record Number (MRN), Hospital Inpatient Number, Hospital Outpatient Number, Social Security Number, Unique Tax Identification Number, Employee Identifier Number, Insurance Policy Number, Insurance Certificate Number, Insurance ID Card Number, Insurance Claim Identifier, Health Plan number, Phone number (e.g., Residential, Official, Mobile Number, etc.), Email identifier, etc. Other attributes that can be useful for comparison in the matching algorithm can include but are not limited to Name (e.g., First name, Middle name, Last name), Date of Birth, Time of Birth, Address (e.g., Official, Residential, Communication address, etc.), Postal Code (e.g., Zip Code), Age, Sex, Marital Status, Blood Group, Race, Religion, etc.

At block 770, the related parties marked as "clear match" and "pending match" against patient records in a clinical system are reviewed by an administrator. Based on review and verification by the administrator, the items are approved (block 780) or rejected (block 785). The approved links from the list identifies the relation/association between patients in the system. These patient-to-patient links can persist in the system for later reference.

In some examples, after the patient linking process has completed its initial run and after possible patient-to-patient relationships have been identified and linked, further changes to patient information in the one or more clinical systems through patient information feeds (HL7-based and/or other) and/or operator entry during Admission/registration, Discharge or Transfer can trigger the integrated linking process (automated and manual). In an integrated linking process, the automated linking process is combined with the manual linking process. Through this process, likely patient matches to the related party are identified when changes happen to existing patient data and/or when new patient data is added. If certain relationships cease to exist or are modified, the patient-to-patient links are updated accordingly. The operator is prompted to approve/reject the match and relationship, and the link is saved/discarded accordingly.

P2P relationships can be aggregated and records linked from a single information system (e.g., a Hospital Information System or Radiology Information System). Data can also be accumulated from several such systems that may follow different database schemas. In such cases, an ETL (Extract, Transform, Load) process can be applied on an Operational Data Store (ODS). Data formats can be cleansed and standardized prior to execution of the linking processes on the ODS, for example.

In some examples, P2P relationships are modeled using a HL7 standards vocabulary. For example, P2P relationships can be modeled using HL7 ver 2.x, according to Data Definition Table #0063. For HL7 v3, the list is more exhaustive and can be found in the vocabulary "RoleCode" (OID—2.16.840.1.113883.5.111). For illustrative purposes, the HL7 v2.5 table #0063—Relationship is reproduced below:

| HL7 2.5 Relationship | | |
|---|---|---|
| Table # | Value | Description |
| 0063 | ASC | Associate |
| 0063 | BRO | Brother |
| 0063 | CGV | Care giver |
| 0063 | CHD | Child |
| 0063 | DEP | Handicapped dependent |
| 0063 | DOM | Life partner |
| 0063 | EMC | Emergency contact |
| 0063 | EME | Employee |
| 0063 | EMR | Employer |
| 0063 | EXF | Extended family |
| 0063 | FCH | Foster child |
| 0063 | FND | Friend |
| 0063 | FTH | Father |
| 0063 | GCH | Grandchild |
| 0063 | GRD | Guardian |
| 0063 | GRP | Grandparent |
| 0063 | MGR | Manager |
| 0063 | MTH | Mother |
| 0063 | NCH | Natural child |
| 0063 | NON | None |
| 0063 | OAD | Other adult |
| 0063 | OTH | Other |
| 0063 | OWN | Owner |
| 0063 | PAR | Parent |
| 0063 | SCH | Stepchild |
| 0063 | SEL | Self |

-continued

| HL7 2.5 Relationship | | |
|---|---|---|
| Table # | Value | Description |
| 0063 | SIB | Sibling |
| 0063 | SIS | Sister |
| 0063 | SPO | Spouse |
| 0063 | TRA | Trainer |
| 0063 | UNK | Unknown |
| 0063 | WRD | Ward of court |

Hospital information systems can store and exchange information on a patient's other related parties. For example, the HL7 v 2.x message structure provides the following segments in ADT (Admissions/Registration, Discharge or Transfer) messages: NK1—Next of Kin/Associated Parties Segment and IAM—Patient Adverse Reaction Information Segment. These segments can be used to link patient records with an information system.

Figure 8:
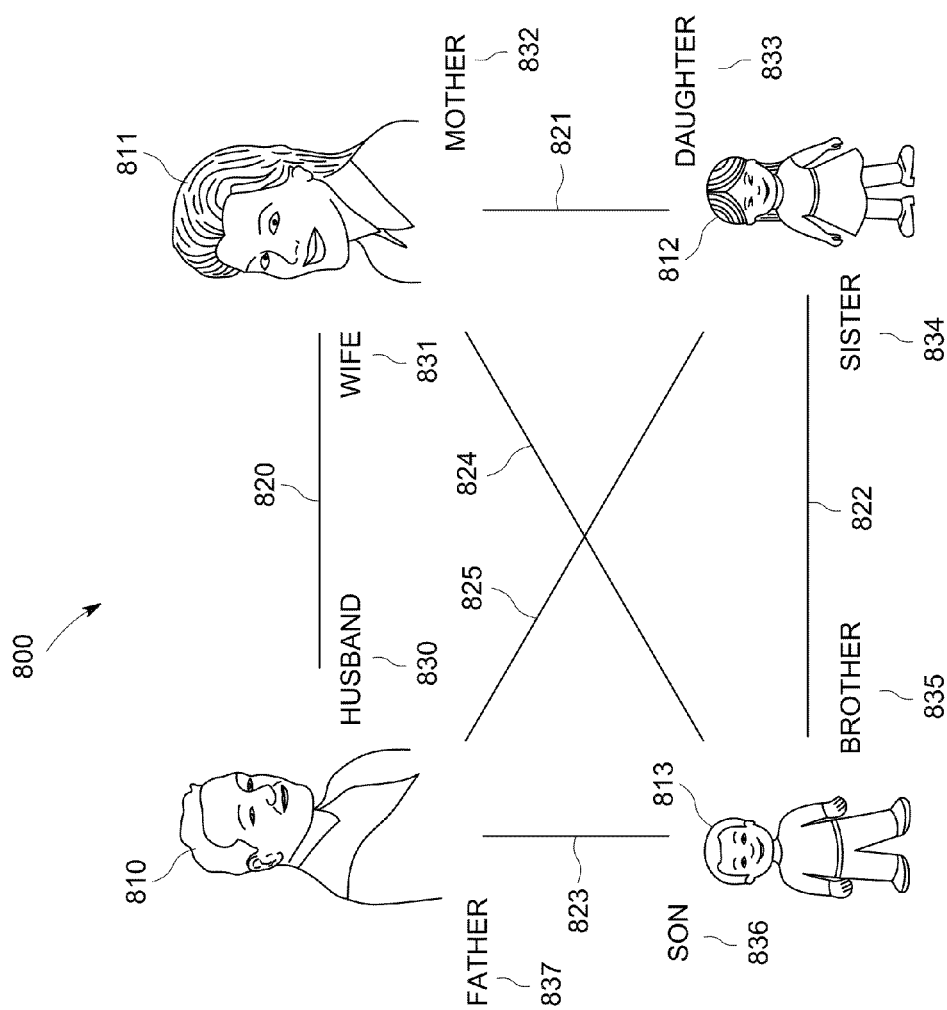
FIG. 8 provides an example user interface displaying and facilitating usage of linked patient to patient (P2P) relationships.

FIG. 8 provides an example user interface 800 displaying and facilitating usage of linked P2P relationships. The user interface 800 shows icons 810-813 (optionally replaced by pictures or miniature representations of the linked individuals or other graphical representations) representing electronic patient records and links 820-825 between those representative icons 810-813. An indication 830-837 of a patient's relationship to another patient (e.g., father, son, brother, sister, mother, daughter, husband, wife) can be provided via the interface 800 as well. By selecting an icon 810-813 and/or a link 820-825 via the interface 800, additional information regarding the patient's record and/or P2P relationship can be retrieved.

Figure 9:
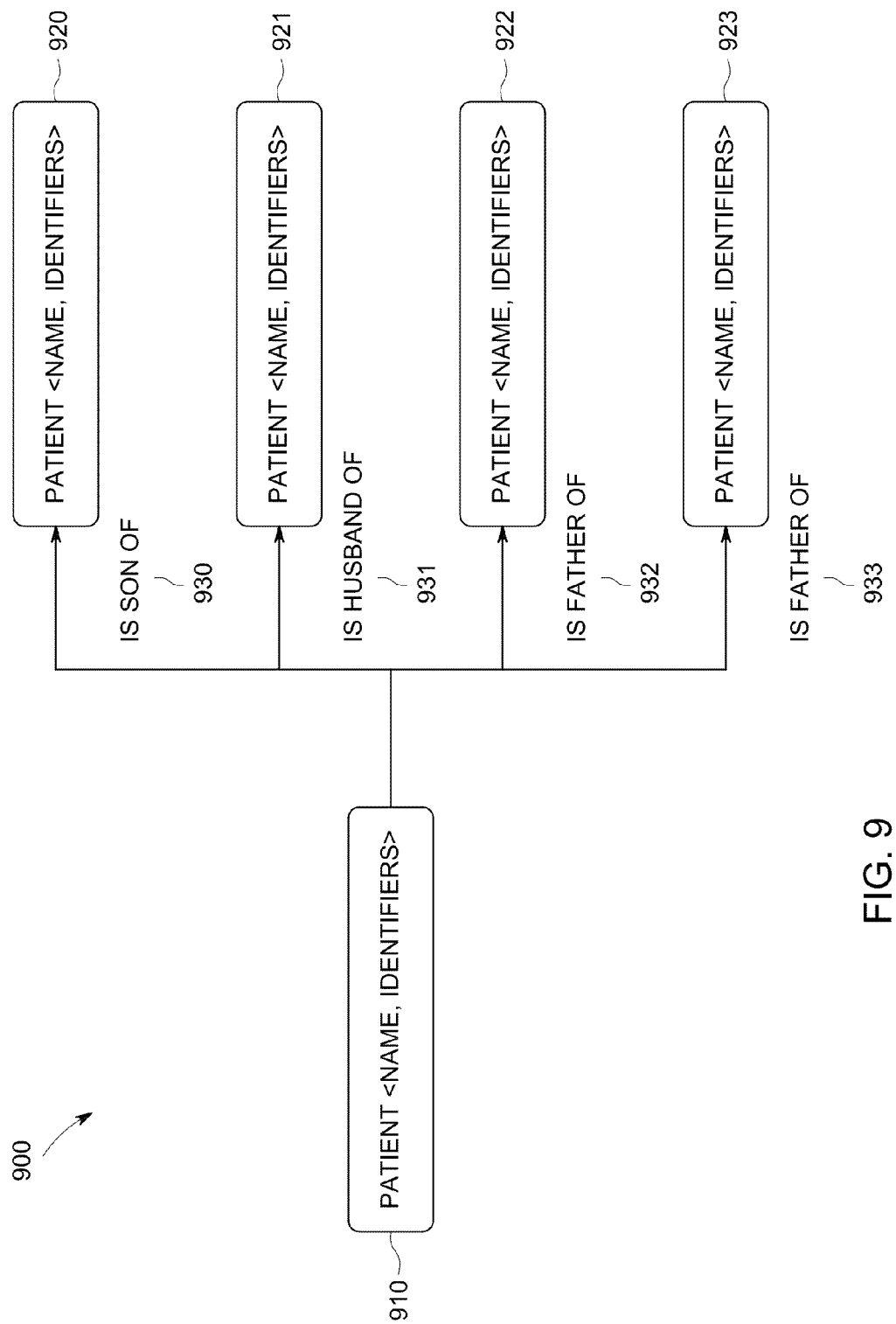
FIG. 9 illustrates an alternate example representation of P2P relationships.

FIG. 9 illustrates an alternate representation 900 of P2P relationships. As shown in FIG. 9, a patient 910 is identified by a name and/or identifier(s). The representation 900 depicts other patients 920-923 that have some relationship to the patient 910. Those patients 920-923 are identified by a name and/or identifier(s). An indication 930-933 of the relationship between the patient 910 and the other patients 920-923 is also provided in the representation 900.

Figure 10:
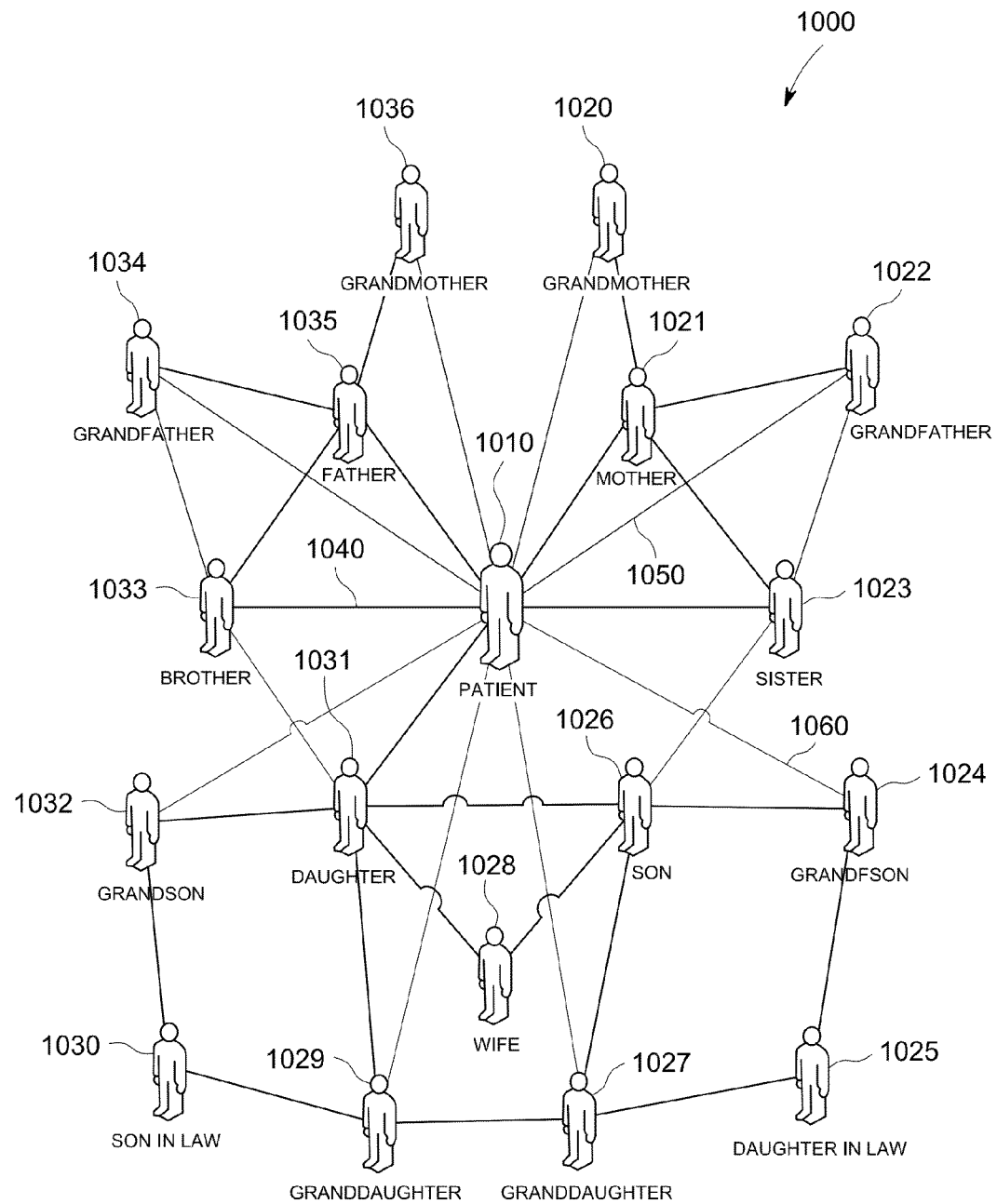
FIG. 10 shows an example user interface providing a depiction of hierarchical relationships with respect to a particular patient.

FIG. 10 shows an example user interface 1000 providing a depiction of hierarchical relationships with respect to a particular patient 1010. In this example, various lines indicate a degree of significance in the relationship between the patient 1010 and the other individual 1020-1036. A thickest line 1040, which can be represented alternatively or in addition with a certain color (e.g., green), indicates relationships that can significantly contribute to a family health history record for the patient. A less thick line 1050, which can be represented alternatively or in addition with another color (e.g., orange), indicates relationships that should be considered moderately to build a family health history for the patient. A thin line 1060, which can be represented alternatively or in addition with another color (e.g., black), indicates relationships that may or may not contribute to a family health history for the patient. By clicking on and/or otherwise selecting an icon 1010, 1020-1036, information regarding that individual can be retrieved (e.g., an electronic medical record and/or other electronic information regarding the person and/or relationship between the person and the patient 1010).

In certain examples, a method 1100 (shown in FIG. 11) is provided to link a patient's unique identifier with his/her family members' identifiers to build a family medical history. The family medical history can be used, for example, to better assist a patient with a family medical history of breast cancer, colorectal cancer, diabetes, heart disease, etc. The family medical history can also be of great use for a pregnant mother concerned with prenatal care and genetics, for example. The family medical history can be a great help to a medical practitioner in gathering information about the risk of disease development, if he/she had access to the detailed family medical history.

The method 1100 facilitates a mechanism to link different members of a family to share their medical records. At block 1110, a registry is provided where members are registered with unique (optionally including substantially unique (e.g., unique to a given facility, enterprise, network, etc.)) identifiers. At block 1120, each member can request a link to another family member and/or other relation by defining a unique hierarchical relationship with him/her. For example, John Doe can enter his information in the registry and can request link to his family members, Jane Doe (sister), Jeff Doe (paternal uncle), and Joanna Doe (mother). The items in parentheses help define the hierarchical relationship between John Doe and the other person. As shown and described in connection with FIG. 9 above, these family members and their hierarchical relationships can be graphically displayed for user (e.g., patient, physician, etc.) viewing and/or selection to retrieve and/or enter additional information.

At block 1130, consent is obtained from linked persons. For example, a person indicated to have a relationship with the patient can receive an electronic message indicating the relationship and requesting acknowledgement of the relationship and/or approval of the connection and associated access to at least certain information to contribute to the family health history. Consent can be facilitated directly via the electronic message and/or by redirection to an electronic interface (e.g., a Web-based interface) to input consent and/or other additional information.

At block 1140, access is provided to linked medical records after consent has been obtained. In some examples, a patient may or may not be able to directly access his family members' medical records. Rather, information can be made available anonymously. Anonymity of the information can be determined on record by record basis, for example.

In some examples, the patient is expected to be affiliated with affinity domain so that the patient can share medical records and establish links between patients. An affinity domain is a group of healthcare enterprises that have agreed to work together using a common set of policies and share a common infrastructure.

Figure 12:
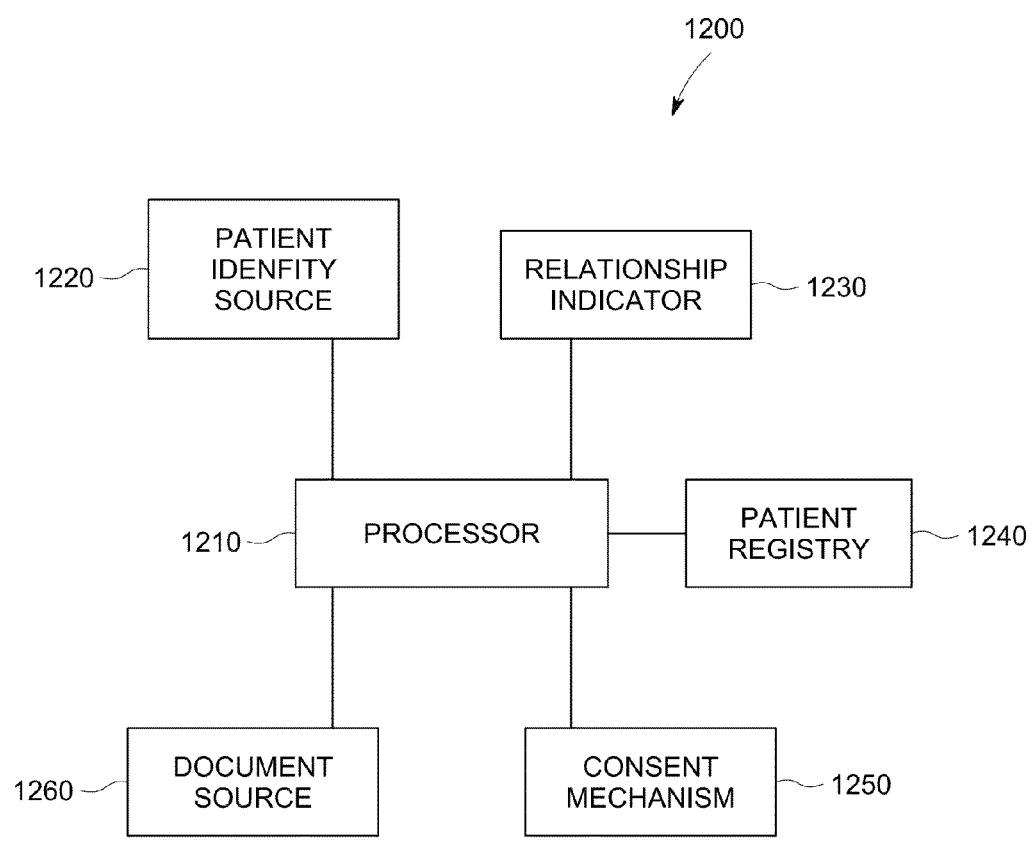
FIG. 12 depicts an example patient relationship identification system to identify and utilize relationships between a patient and other persons with electronic medical data available.

FIG. 12 depicts an example patient relationship identification system 1200 to identify and utilize relationships between a patient and other persons with electronic medical data available. The system includes a processor 1210 that processes patient electronic medical information to identify relationships between patients and provide links between records. A patient identity source 1220 generates patient identifiers. A (hierarchical) relationship indicator 1230 helps examine and evaluate a significance of a family member's and/or other related person's medical history on the patient's medical records. A patient registry 1240 is used to register the patient identifiers and link the identifiers. An identifier can also be useful to pull and/or synchronize information among multiple sources, for example. Patients can be associated with an affinity domain to help facilitate linking and sharing of information, for example. IHE's XDS profile(s)/protocol(s) can be used to share and/or connect documents between systems and/or facilities, for example. Using IHE profile(s)/protocol(s), such as XDS, a document format standard can be defined to search and/or identify information in the shared/connected documents, for example.

The system 1200 can also include a consent mechanism 1250 to obtain family member and/or other related person's approval to share their medical records once they receive a request to become linked to a patient. Additionally, a document source 1260 such as a PACS, RIS, EMR, EHR, PHR, and/or other electronic data source can be used to provide and access medical records, for example.

Using the system 1200, patients can be linked to build more comprehensive family and/or other relationship (e.g., working environment, geographical, etc.) medical histories to aid in the diagnosis and/or treatment of patients. As a patient becomes aware of a connection within his or her family or relationship hierarchy, he or she may seek to gather additional personal information regarding his or her risk to develop particular diseases. With important information conveniently available to healthcare providers, a hospital and/or other healthcare enterprise can improve efficiency of care delivery. Linked electronic medical records can be used by the system 1200 to provide an ability to track and trend various set(s) of information based on wider access to personal medical records collected from several sources of information, for example.

In some examples, medical data is stored and accessed in a patient-centric manner as well as via links or relationships between certain patients. A "family link" and/or a "relationship link" can be used to electronically link different patients together, both from an electronic storage perspective as well as a system presentation perspective. A patient can request and approve "links" to parents, sibling, children, and/or other related individuals, for example. Links can be used to import and/or establish a searchable connection to electronic medical information such as that found in a clinical system, EMR, EHR, PHR, etc. In some examples, a request to establish a link must be mutually agreed upon by the parties involved.

In some examples, links may not be limited to family member links. For example, two patients dealing with similar problems may choose to link to each other so that a primary physician can track the treatments and progress for each patient and compare the results. In some examples, more than two people can link to each other to provide a group link instead of and/or in addition to a person-to-person relationship link.

Once an approved link is in place, a clinician, such as a physician, is approved to access linked records when the clinician accesses a patient's medical information. The linked information (e.g., parent, sibling, and/or child information, etc.) can be leveraged by the clinician in the course of a patient's treatment, for example.

Linked information can be used to provide an early indicator of one or more health ailments, for example. Using linked information, a clinician can help apply preventative measures to address a patient's predisposition for a particular disease or ailment, for example.

In some examples, a link between different patients can be maintained in a cross reference table in a database. Link approvals can be maintained in the database and can be updated if an individual chooses to opt out at a later date.

When viewing a patient record in a clinical system, for example, data from linked patients can be leveraged to provide up-to-date electronic information on demand. Treatments can be cross-checked against linked patients to determine if an adverse condition may apply. Early health recommendations can be presented to make the clinician aware of one or more possible conditions for the patient, for example. In some examples, data can be leveraged and presented to not only the clinician but also to the patient through, for example, a PHR system. Other systems, such as an in-patient clinical system, an out-patient EMR system, a lab system, etc., can provide linked data to a patient and/or clinician, for example.

Thus, certain examples can assist a medical practitioner in gathering information about the risk of disease development for a patient based on a more detailed family medical history and/or other related information. With multiple data points in distributed systems such as EMR, PHR, PACS, etc., certain examples can be helpful in bringing information together to review a plurality of applicable records for patient care. Certain examples can be integrated with systems such as a PACS, RIS, PHR, EMR, EHR, etc., (e.g., a GE Centricity® PACS, EMR, etc.) to obtain and/or link medical records. A hierarchy can be introduced into patient relationships to emphasize/de-emphasize condition relevance, etc.

Certain examples aggregate patient relationship information in a particular hospital information system and/or across several such systems. A graphical representation of the relationship tree, for example, is provided for easy visualization of the relationship(s). Alerts cam be generated for operators based on the relationship of a patient with other patients at various points in a patient care workflow (e.g., registration, ADT, etc.), as configured by an administrator, user, default, etc. Further, in addition to routine patient diagnosis and treatment, certain examples enable the utilization of relationship information during emergencies, clinical studies, clinical analysis, etc. In certain examples, health records organized based on relationship can be accessed as part of a patient online portal (e.g., VPN and/or Web-accessible portal, etc.).

Figure 13:
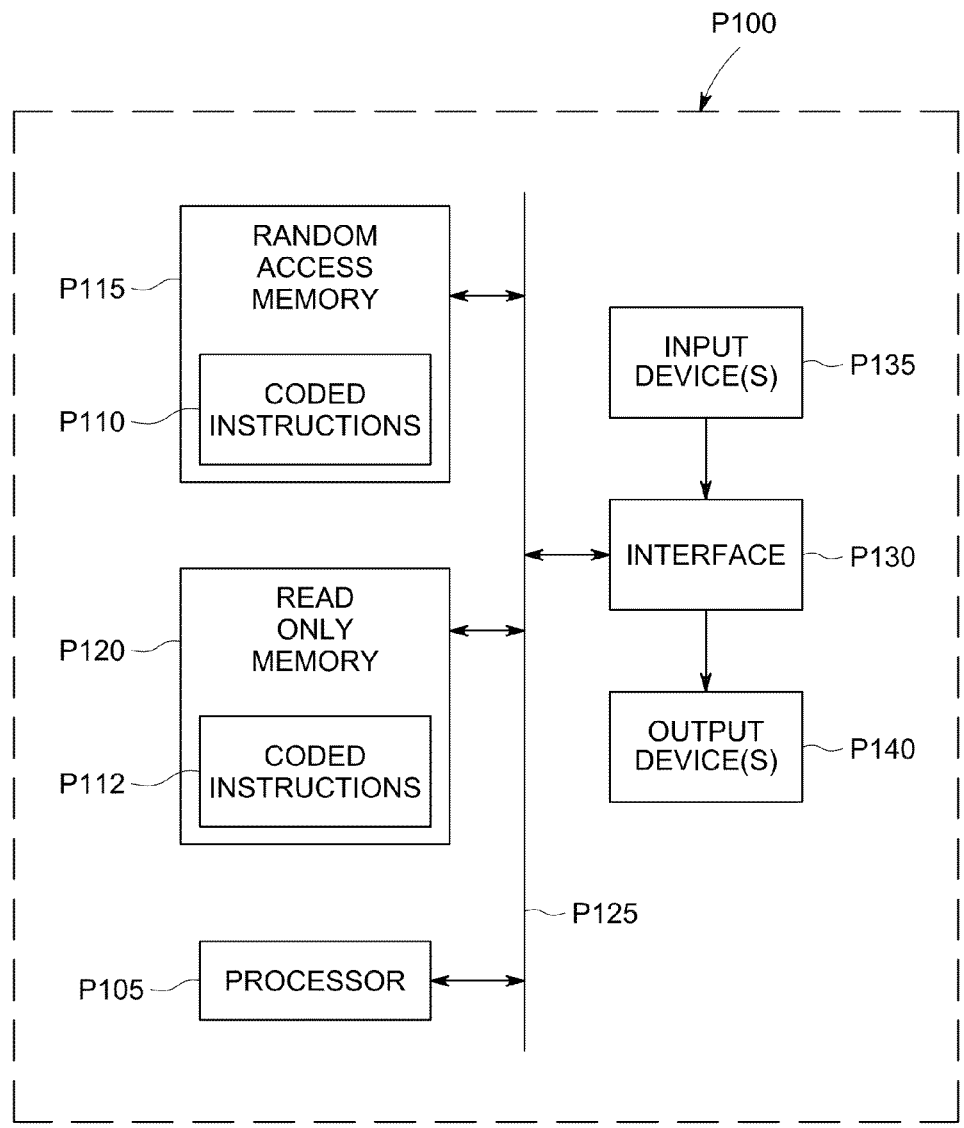
FIG. 13 is a schematic diagram of an example processor platform that may be used and/or programmed to implement the example systems, apparatus, articles of manufacture, and methods described herein.

FIG. 13 is a schematic diagram of an example processor platform P100 that may be used and/or programmed to implement the example systems, apparatus, articles of manufacture, and methods described herein. For example, the processor platform P100 can be implemented by one or more general-purpose processors, processor cores, microcontrollers, etc., which can become particular or special machines through programming and/or configuration based on systems and methods described herein.

The processor platform P100 of the example of FIG. 13 includes at least one general-purpose programmable processor P105. The processor P105 executes coded instructions P110 and/or P112 present in main memory of the processor P105 (e.g., within a RAM P115 and/or a ROM P120). The processor P105 may be any type of processing unit, such as a processor core, a processor and/or a microcontroller. The processor P105 may execute, among other things, the example process of FIGS. 7 and 11 to implement the example methods, systems, apparatus, and articles of manufacture described herein.

The processor P105 is in communication with the main memory (including a ROM P120 and/or the RAM P115) via a bus P125. The RAM P115 may be implemented by dynamic random access memory (DRAM), synchronous dynamic random access memory (SDRAM), and/or any other type of RAM device, and ROM may be implemented by flash memory and/or any other desired type of memory device. Access to the memory P115 and the memory P120 may be controlled by a memory controller (not shown). The example memory P115 may be used to implement the example data stores described herein.

The processor platform P100 also includes an interface circuit P130. The interface circuit P130 may be implemented by any type of interface standard, such as an external memory interface, serial port, general-purpose input/output, etc. One or more input devices P135 and one or more output devices P140 are connected to the interface circuit P130. The input devices P135 may be used to, for example, receive patient documents from a remote PHR server and/or database. The example output devices P140 may be used to, for example, provide patient documents for review and/or storage at a remote PHR server and/or database.

Certain examples above can be applied to an architecture and components based upon Health Information Exchange (HIE) standards, such as document storage, querying, etc. Certain examples provide Web portal applications for data presentation to patients. A Web-based portal can provide an adaptive and proactive experience for users including matching technology/tools, education/information, and guided feedback based upon a patient's specific personality and lifestyle assessment, for example.

Figure 14:
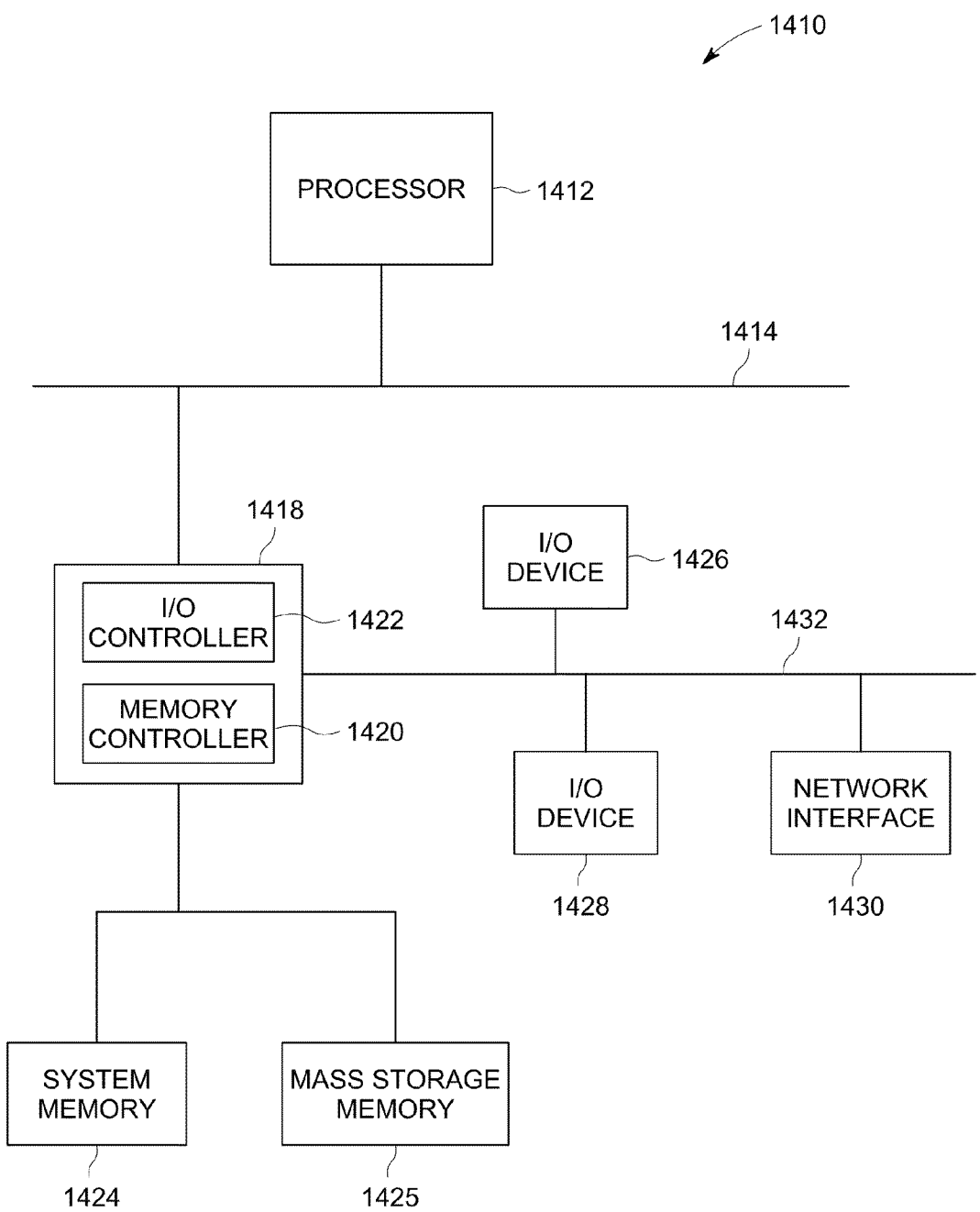
FIG. 14 is a block diagram of an example processor system that may be used to implement systems, apparatus, articles of manufacture, and methods described herein.

FIG. 14 is a block diagram of an example processor system 1410 that may be used to implement systems, apparatus, articles of manufacture, and methods described herein. As shown in FIG. 14, the processor system 1410 includes a processor 1412 that is coupled to an interconnection bus 1414. The processor 1412 may be any suitable processor, processing unit, or microprocessor, for example. Although not shown in FIG. 14, the system 1410 may be a multi-processor system and, thus, may include one or more additional processors that are identical or similar to the processor 1412 and that are communicatively coupled to the interconnection bus 1414.

The processor 1412 of FIG. 14 is coupled to a chipset 1418, which includes a memory controller 1420 and an input/output (I/O) controller 1422. As is well known, a chipset typically provides I/O and memory management functions as well as a plurality of general purpose and/or special purpose registers, timers, etc. that are accessible or used by one or more processors coupled to the chipset 1418. The memory controller 1420 performs functions that enable the processor 1412 (or processors if there are multiple processors) to access a system memory 1424 and a mass storage memory 1425.

The system memory 1424 may include any desired type of volatile and/or non-volatile memory such as, for example, static random access memory (SRAM), dynamic random access memory (DRAM), flash memory, read-only memory (ROM), etc. The mass storage memory 1425 may include any desired type of mass storage device including hard disk drives, optical drives, tape storage devices, etc.

The I/O controller 1422 performs functions that enable the processor 1412 to communicate with peripheral input/output (I/O) devices 1426 and 1428 and a network interface 1430 via an I/O bus 1432. The I/O devices 1426 and 1428 may be any desired type of I/O device such as, for example, a keyboard, a video display or monitor, a mouse, etc. The network interface 1430 may be, for example, an Ethernet device, an asynchronous transfer mode (ATM) device, an 802.11 device, a DSL modem, a cable modem, a cellular modem, etc. that enables the processor system 1410 to communicate with another processor system.

While the memory controller 1420 and the I/O controller 1422 are depicted in FIG. 14 as separate blocks within the chipset 1418, the functions performed by these blocks may be integrated within a single semiconductor circuit or may be implemented using two or more separate integrated circuits.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example.

Some or all of the system, apparatus, and/or article of manufacture components described above, or parts thereof, can be implemented using instructions, code, and/or other software and/or firmware, etc. stored on a machine accessible or readable medium and executable by, for example, a processor system (e.g., the example processor P105 of FIG. 13 and/or the processor 1412 of FIG. 14). When any of the appended claims are read to cover a purely software and/or firmware implementation, at least one of the components in at least one example is hereby expressly defined to include a tangible medium such as a memory, DVD, CD, etc. storing the software and/or firmware.

Figure 11:
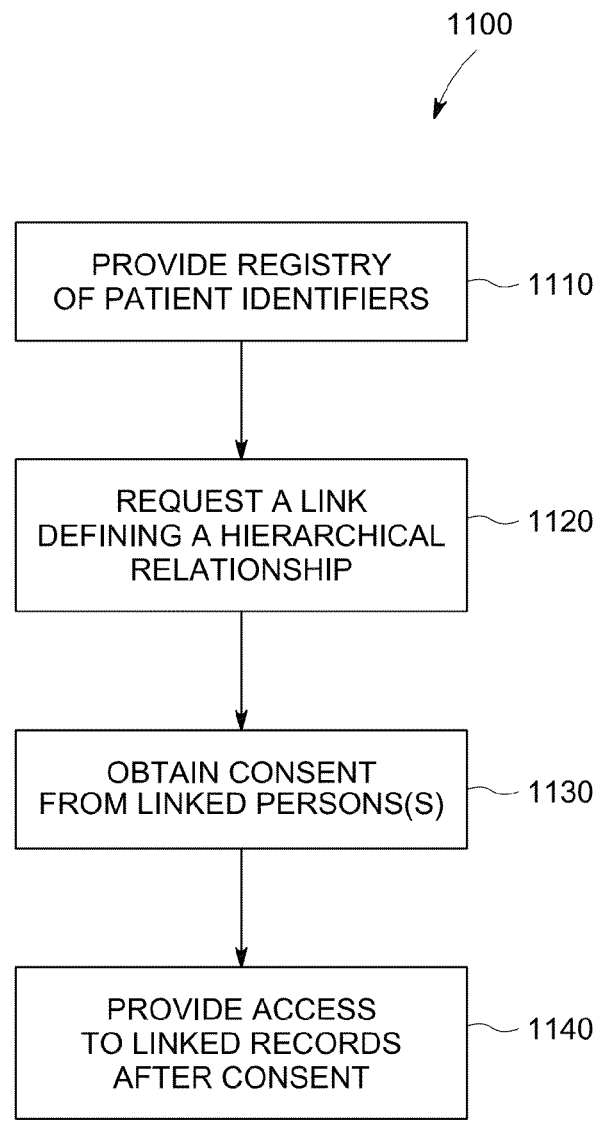
FIG. 11 shows a flow diagram for an example method to link a patient's unique identifier with his/her family members' identifiers to build a family medical history.

FIGS. 7 and 11, for example, include flow diagrams representative of machine readable and executable instructions or processes that can be executed to implement the example systems, apparatus, and article of manufacture described herein. The example processes of FIGS. 7 and 11 can be performed using a processor, a controller and/or any other suitable processing device. For example, the example processes of FIGS. 7 and 11 can be implemented in coded instructions stored on a tangible medium such as a flash memory, a read-only memory (ROM) and/or random-access memory (RAM) associated with a processor (e.g., the processor P105 of FIG. 13 and/or the processor 1412 of FIG. 14). Alternatively, some or all of the example processes of FIGS. 7 and 11 can be implemented using any combination(s) of application specific integrated circuit(s) (ASIC(s)), programmable logic device(s) (PLD(s)), field programmable logic device(s) (FPLD(s)), discrete logic, hardware, firmware, etc. Also, some or all of the example processes of FIGS. 7 and 11 can be implemented manually or as any combination(s) of any of the foregoing techniques, for example, any combination of firmware, software, discrete logic and/or hardware. Further, although the example processes of FIGS. 7 and 11 are described with reference to the flow diagrams of FIGS. 7 and 11, other methods of implementing the processes of FIGS. 7 and 11 can be employed. For example, the order of execution of the blocks may be changed, and/or some of the blocks described may be changed, eliminated, sub-divided, or combined. Additionally, any or all of the example processes of FIGS. 7 and 11 can be performed sequentially and/or in parallel by, for example, separate processing threads, processors, devices, discrete logic, circuits, etc.

One or more of the components of the systems and/or blocks of the methods described above may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device. Certain embodiments of the present invention may omit one or more of the method blocks and/or perform the blocks in a different order than the order listed. For example, some blocks may not be performed in certain embodiments of the present invention. As a further example, certain blocks may be performed in a different temporal order, including simultaneously, than listed above.

Certain embodiments include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of embodiments of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated computer-readable media provide nonvolatile storage of computer-executable instructions, data structures, program modules and other data for the computer.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. An apparatus providing access to electronic health information for a first patient and one or more patients connected by relationship to the first patient, said apparatus comprising:
   a processor and a memory arranged to implement a hierarchical patient relationship tree graphical user interface, the interface comprising:
   a first graphical patient indicator representing a first patient and providing a link to electronic health information for said first patient, said electronic health information to be accessible to a user by selecting said first patient indicator;
   a second graphical patient indicator representing a second patient and providing a link to electronic health information for said second patient;
   a connection providing a graphical indication of a patient-to-patient relationship between said first patient and said second patient and connecting electronic health information for said second patient for access in connection with electronic health information for said first patient, said connection to provide a graphical indication of a priority of the relationship between said first patient and said second patient based on a defined relationship hierarchy; and
   a graphical indication of a type of the patient-to-patient relationship between said first patient and said second patient,
   wherein said first patient indicator, said second patient indicator, said connection, and said graphical relationship indicator are displayed for user selection and interaction together via the hierarchical patient relationship tree interface via a display via a user interface,
   wherein each connection in the hierarchical patient relationship tree is to visually and electronically associate the first patient with at least the second patient and to electronically link the hierarchical patient relationship tree to electronic medical information records for the first patient and the second patient, the hierarchical patient relationship tree navigable by selecting, via the interface, the indicators connected visually in the hierarchical patient relationship tree and displayed via the interface according to the relationship between the patients.

2. The apparatus of claim 1, wherein said connection graphically indicates said priority of the relationship between said first patient and said second patient using a color in a displayed line linking said first patient indicator and said second patient indicator.

3. The apparatus of claim 1, wherein said connection graphically indicates said priority of the relationship between said first patient and said second patient using a thickness in a displayed line linking said first patient indicator and said second patient indicator.

4. The apparatus of claim 1, wherein said apparatus is incorporated into an electronic medical records system.

5. The apparatus of claim 1, further comprising a patient registry identifying said first patient and said second patient, said patient registry accessible to a user via said user interface.

6. The apparatus of claim 1, further comprising clinical decision support provided for said first patient based on electronic health information for said first patient and electronic health information for said second patient, wherein said clinical decision support weights electronic health information from said second patient based on said priority associated with said relationship between said first patient and said second patient.

7. The apparatus of claim 1, wherein electronic health information for said first patient and said second patient is associated with an affinity domain.

8. The apparatus of claim 1, wherein said connection is established between said first patient and said second patient based on consent from at least one of said first patient and said second patient.

9. A tangible computer-readable storage medium including a set of instructions for execution on a processor, the set of instructions, when executed, implement a system for graphical display of and access to electronic health information for a first patient and one or more patients connected by relationship to the first patient, said system comprising:
 a hierarchical patient relationship tree graphical user interface comprising:
  a first graphical patient indicator representing a first patient and providing a link to electronic health information for said first patient, said electronic health information to be accessible to a user by selecting said first patient indicator;
  a second graphical patient indicator representing a second patient and providing a link to electronic health information for said second patient;
  a connection providing a graphical indication of a patient-to-patient relationship between said first patient and said second patient and connecting electronic health information for said second patient for access in connection with electronic health information for said first patient, said connection to provide a graphical indication of a priority of the relationship between said first patient and said second patient based on a defined relationship hierarchy; and
  a graphical indication of a type of the patient-to-patient relationship between said first patient and said second patient,
  wherein said first patient indicator, said second patient indicator, said connection, and said graphical relationship indicator are displayed for user selection and interaction together via the hierarchical patient relationship tree interface via a display via a user interface,
  wherein each connection in the hierarchical patient relationship tree is to visually and electronically associate the first patient with at least the second patient and to electronically link the hierarchical patient relationship tree to electronic medical information records for the first patient and the second patient, the hierarchical patient relationship tree navigable by selecting, via the interface, the indicators connected visually in the hierarchical patient relationship tree and displayed via the interface according to the relationship between the patients.

10. The computer-readable storage medium of claim 9, wherein said connection graphically indicates said priority of the relationship between said first patient and said second patient using a color in a displayed line linking said first patient indicator and said second patient indicator.

11. The computer-readable storage medium of claim 9, wherein said connection graphically indicates said priority of the relationship between said first patient and said second patient using a thickness in a displayed line linking said first patient indicator and said second patient indicator.

12. The computer-readable storage medium of claim 9, further comprising clinical decision support provided for said first patient based on electronic health information for said first patient and electronic health information for said second patient, wherein said clinical decision support weights electronic health information from said second patient based on said priority associated with said relationship between said first patient and said second patient.

13. The computer-readable storage medium of claim 9, wherein electronic health information for said first patient and said second patient is associated with an affinity domain.

14. The computer-readable storage medium of claim 9, wherein said connection is established between said first patient and said second patient based on identification of one or more commonalties between said first patient and said second patient and is dependent upon consent from at least one of said first patient and said second patient.

15. A computer-implemented method for graphically displaying and providing access to electronic health information for a first patient and one or more patients connected by relationship to the first patient, said method comprising:
 generating and displaying, via a hierarchical patient relationship tree graphical user interface using a processor, a first graphical patient indicator representing a first patient and providing a link to electronic health information for said first patient, said electronic health information to be accessible to a user by selecting said first patient indicator;
 generating and displaying, via the hierarchical patient relationship tree interface using a processor, a second graphical patient indicator representing a second patient and providing a link to electronic health information for said second patient;
 providing, via the hierarchical patient relationship tree interface using a processor, a graphical indication of a patient-to-patient relationship between said first patient and said second patient using a graphical connection between said first patient indicator and said second patient indicator and linking electronic health information for said second patient for access in connection with electronic health information for said first patient, said connection to provide a graphical indication of a priority of the relationship between said first patient and said second patient based on a defined relationship hierarchy; and
 generating and displaying, via the hierarchical patient relationship tree interface using a processor, a graphical indication of a type of the patient-to-patient relationship between said first patient and said second patient,
 wherein said first patient indicator, said second patient indicator, said connection, and said graphical relationship indicator are displayed for user selection and interaction together via the hierarchical patient relationship tree interface via a display via a user interface,
 wherein each connection in the tree is to visually and electronically associate the first patient with at least the second patient and to electronically link the hierarchical patient relationship tree to electronic medical information record for the first patient and the second patient, the hierarchical patient relationship tree navigable by selecting, via the interface, the indicators connected visually in the hierarchical patient relationship tree and displayed via the interface according to the relationship between the patients.

16. The method of claim 15, wherein said connection graphically indicates said priority of the relationship between said first patient and said second patient using a color in a displayed line linking said first patient indicator and said second patient indicator.

17. The method of claim 15, wherein said connection graphically indicates said priority of the relationship between said first patient and said second patient using a thickness in a displayed line linking said first patient indicator and said second patient indicator.

18. The method of claim 15, further comprising providing clinical decision support for said first patient based on electronic health information for said first patient and electronic health information for said second patient, wherein said clinical decision support weights electronic health information from said second patient based on said priority associated with said relationship between said first patient and said second patient.

19. The method of claim 15, wherein electronic health information for said first patient and said second patient is associated with an affinity domain.

20. The method of claim 15, wherein said connection is established between said first patient and said second patient based on identification of one or more commonalties between said first patient and said second patient and is dependent upon consent from at least one of said first patient and said second patient.

* * * * *